(12) United States Patent
Lee et al.

(10) Patent No.: US 9,708,650 B2
(45) Date of Patent: *Jul. 18, 2017

(54) CHEMICALLY-ENHANCED PRIMER COMPOSITIONS, METHODS AND KITS

(71) Applicant: LIFE TECHNOLOGIES CORPORATION, Carlsbad, CA (US)

(72) Inventors: Linda Lee, Palo Alto, CA (US); Sam Woo, Redwood City, CA (US); Peter Ma, Cupertino, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 240 days.

This patent is subject to a terminal disclaimer.

(21) Appl. No.: 14/198,308

(22) Filed: Mar. 5, 2014

(65) Prior Publication Data

US 2014/0377747 A1  Dec. 25, 2014

Related U.S. Application Data

(63) Continuation of application No. 13/397,626, filed on Feb. 15, 2012, now Pat. No. 8,703,925, which is a continuation-in-part of application No. 13/284,839, filed on Oct. 28, 2011, now abandoned.

(60) Provisional application No. 61/407,899, filed on Oct. 28, 2010, provisional application No. 61/408,553, filed on Oct. 29, 2010.

(51) Int. Cl.
*C12Q 1/68* (2006.01)
*C12P 19/34* (2006.01)

(52) U.S. Cl.
CPC .......... *C12Q 1/686* (2013.01); *C12Q 1/6869* (2013.01); *C12Q 1/6874* (2013.01)

(58) Field of Classification Search
CPC ..................................................... C12Q 1/686
USPC ................................................ 435/6.1, 91.1
See application file for complete search history.

(56) References Cited

U.S. PATENT DOCUMENTS

| | | | |
|---|---|---|---|
| 5,518,900 A | 5/1996 | Nikiforov et al. | |
| 5,741,676 A | 4/1998 | Fuller | |
| 5,756,285 A | 5/1998 | Fuller | |
| 5,849,487 A | 12/1998 | Hase et al. | |
| 6,379,940 B2 | 4/2002 | Moffett et al. | |
| 6,387,634 B2 | 5/2002 | Moffett et al. | |
| 6,436,635 B1 | 8/2002 | Fu et al. | |
| 8,211,673 B2 | 7/2012 | Lee | |
| 8,703,925 B2 | 4/2014 | Lee et al. | |
| 2004/0126765 A1 | 7/2004 | Adams | |
| 2006/0141487 A1 | 6/2006 | Ma et al. | |
| 2008/0131937 A1 | 6/2008 | Schroeder | |
| 2009/0035777 A1 | 2/2009 | Kokoris et al. | |
| 2009/0215062 A1 | 8/2009 | Lee | |
| 2012/0270211 A1 | 10/2012 | Lee et al. | |

FOREIGN PATENT DOCUMENTS

| | | |
|---|---|---|
| EP | 2274441 | 6/2012 |
| EP | 2489744 | 8/2012 |
| WO | 99/34014 | 7/1999 |
| WO | 2005/040425 | 5/2005 |
| WO | 2006/073892 | 7/2006 |
| WO | 2009/100080 | 8/2009 |
| WO | 2012/058647 | 5/2012 |

OTHER PUBLICATIONS

Gale, James et al., "Evaluation of 15 Polymerases and Phosphorothioate Primer Modification for Detection of UV-induced C:G to T:A Mutations by Allele-specific PCR", *Photochemistry and Photobiology*, 79(5), 2004, 461-469.

Lutz, M. t al., "Recognition of Uncharged Polyamide-Linked Nucleic Acid Analogs by DNA Polymerases and Reverse Transcriptases", *JAm. Chem. Soc*, 119, 1997, 3177-3178.

Skerra, "Phosphorothioate Primers Improve the Amplification of DNA Sequences by DNA Polymerases with Proofreading Activity", *Nucleic Acids Research*, vol. 20(14), 1992, 3551-3554.

EP Appl. No. 12160828.5; Extended European Search Report mailed Jul. 18, 2012, 4 pages.

Bannwarth, Willi et al., "Short Optimally Capped Duplex DNA as Conformationally Restricted Analogue of B-DNA", *Helvetica Chimica Acta*, vol. 77, No. 1, Feb. 1994, 182-193.

De Noronha, C.M. et al., "Amplimers with 3'-terminal phosphorothioate linkages resist degradition by vent polymerase and reduce Taq polymerase mispriming", *Genome Research*, vol. 2, 1992, 131-136.

Dean, F.B. et al., "Rapid amplification of plasmid and phage DNA using Phi 29 DNA polymerase and multiply-primed rolling circle amplification", *Genome Research*, Jun. 2001, 1095-1099.

Di Giusto, D. et al., "Single base extension (SBE) with proofreading polymerases and phosphorothioate primers: improved fidelity in single-substrate assays", *Nucleic Acids Research*, vol. 31, No. 3 e7, 2003, 12 pages.

Kim, J. et al., "One-Step Enzymatic Purification of PCR Products for Direct Sequencing", *Current Protocols in Human Genetics*, John Wiley & Sons, Inc., Aug. 2001, 11.6.1-11.6.4.

PCT/US2009/032989; International Preliminary Report on Patentability mailed Aug. 19, 2010, 7 pages.

PCT/US2009/032989; International Search Report and the Written Opinion mailed Jun. 22, 2009, 28 pages.

(Continued)

*Primary Examiner* — Jezia Riley

(57) ABSTRACT

A chemically-enhanced primer is provided comprising a negatively charged moiety (NCM), an oligonucleotide sequence having a) non-nuclease resistant inter-nucleotide linkages or b) at least one nuclease resistance inter-nucleotide linkage. The chemically-enhanced primer can be used for sequencing and fragment analysis. Methods for synthesizing the chemically-enhanced primer as well as a method of preparing DNA for sequencing, a method of sequencing DNA, and kits containing the chemically-enhanced primer are also provided. The method of sequencing DNA can comprise contacting amplification reaction products with the composition wherein excess amplification primer is degraded by the nuclease and the chemically-enhanced primer is essentially non-degraded.

9 Claims, 8 Drawing Sheets

(56) References Cited

OTHER PUBLICATIONS

PCT/US2011/058474; International Preliminary Report on Patentability mailed Apr. 30, 2013, 8 pages.
PCT/US2011/058474; International Search Report and Written Opinion mailed Feb. 26, 2012, 71 pages.
Richardson, Paul L. et al., "Tethered oligonucleotide probes. A strategy for the recognition of structured RNA", *Journal of the American Chemical Society*, vol. 113, No. 13, American Chemical Society, Jun. 1991, 5109-5111.
Slatko, Barton E. et al., "DNA Sequencing by the Dideoxy Method", *Current Protocols in Molecular Biology*, John Wiley & Sons, Inc., 1999, 7.4A1-7.4A.39.
USB Corporation, "PCR Product Pre-Sequencing Kit", downloaded from www.usbweb.com, Product No. 70995, 70996 and 70997, 2007, 10 pages.

*Phosphorothioate linkage

Phosphorothioate oligonucleotide $(C3)_{10}$ M13-forward (C3)₈ M13-forward (C3)₉ M13-forward (C3)₅ M13-forward (C3)₈-treb-M13-forward (C3)$_{15}$-M13*(forward)
Template ZC
*: phosphorothioate (C3)$_{15}$-M13*(forward)
Template Seq01
*: phosphorothioate (C3)$_{15}$-M13*(forward)
Template RSA000317141
*: phosphorothioate (C3)₁₅ -gene specific primer oligonucleotide sequence*(forward)
*: phosphorothioate (C3)₁₅ -universal primer oligonucleotide sequence*(forward)
*: phosphorothioate (C3)₁₅ -oligonucleotide sequence-forward

CHEMICALLY-ENHANCED PRIMER COMPOSITIONS, METHODS AND KITS

CROSS-REFERENCE TO RELATED APPLICATIONS

This application is a continuation of U.S. application Ser. No. 13/397,626, filed Feb. 15, 2012, now U.S. Pat. No. 8,703,925, which is a continuation-in-part of U.S. application Ser. No. 13/284,839, filed Oct. 28, 2011, which claims the benefit under 35 U.S.C. 119(e) of U.S. Provisional Patent Application No. 61/407,899, filed Oct. 28, 2010, and of U.S. Provisional Patent Application No. 61/408,553, filed Oct. 29, 2010, and wherein each disclosure of the foregoing is incorporated herein by reference in its entirety.

FIELD

The present teachings pertain to chemically modified oligonucleotide sequence primer compositions and methods for sequencing DNA and fragment analysis. The teachings also relate to compositions for preparing, fragment analysis and sequencing of nucleic acids such as cDNA and DNA.

BACKGROUND

A standard polymerase chain reaction (PCR)/sequencing workflow generally includes five steps requiring reagent addition: an initial PCR step, a PCR clean-up step, a sequencing step, a sequencing cleanup step, and electrophoresis. The PCR step involves amplification of a template polynucleotide using amplification primers and a thermostable DNA polymerase enzyme. The PCR cleanup step is commonly done by the addition of exonuclease I and alkaline phosphatase, followed by incubation, and subsequent heat-inactivated to inactivate the enzymes. A standard PCR/sequencing workflow is illustrated in FIG. 1A.

A typical PCR reaction uses an excess of amplification primers, some primers remain unincorporated upon completion of the PCR reaction. This necessitates removal of the excess primers before proceeding to a sequencing reaction, because the excess amplification primers will interfere with the subsequent sequencing reaction. The PCR reaction furthermore contains an excess of dNTPs that can interfere with the subsequent sequencing reaction. The hydrolytic properties of exonuclease I which degrades single-stranded DNA present in the PCR mixture allows the amplification product (amplicon) to be used more efficiently in subsequent sequencing applications. The enzyme activity of alkaline phosphatase dephosphorylates free dNTPs remaining from the PCR reaction. After an appropriate incubation period, the exonuclease I and alkaline phosphatase enzymes are heat inactivated before adding sequencing primer, dNTPs, and dye-labeled ddNTPs; otherwise the enzymes would degrade these reagents and the sequencing reaction products.

Without adequate exonuclease I treatment to remove excess PCR amplification primers, aberrant sequence ladders can be generated. An excess of dNTPs can produce a weak sequencing signal and/or short sequence reads. The need to obtain high quality sequence results at base 1 from the sequencing primer is also often difficult. The transition from amplification to efficient sequencing has made high quality 5' sequence resolution and clean-up of unincorporated dNTPs and amplification primers a priority to obtain clean sequencing results.

Resolution of nucleic acid sequence near the sequencing primer has been difficult to obtain without sacrificing throughput residence time during electrophoresis with POP7™ polymer. Adjustments in the type of mobility system, for example, using the POP6™ polymer matrix, adjusting denaturing conditions and temperature can improve resolution but always at the expense of increased electrophoresis time as POP6 polymer requires longer electrophoresis time. Difficulties in removal of unincorporated reactants and long residence time when performing size-dependent mobility separation contribute to inefficiencies in nucleic acid sequencing. A need exists for improved methods for the PCR/sequencing and PCR/fragment analysis workflow and sequence resolution following PCR amplification.

SUMMARY

In one aspect, the invention provides a chemically-enhanced primer comprising: an oligonucleotide sequence having a) non-nuclease resistant inter-nucleotide linkages or b) at least one nuclease resistance inter-nucleotide linkage; and a negatively charged moiety (NCM). In some embodiments, the chemically-enhanced primer includes a NCM having a structure of the formula:

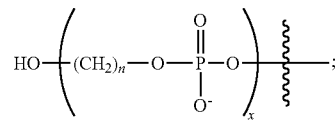

where each instance of n is independently an integer of 1 to 9; and x is an integer of 1 to about 30. In some embodiments, the chemically-enhanced primer has a structure of Formula IV:

Formula IV

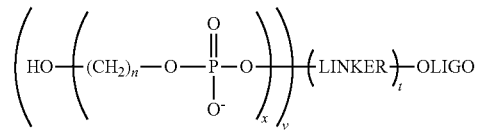

where each instance of n is independently an integer of 1 to 9; x is an integer of 1 to 50; v is an integer of 1 to 9; t is 0 or 1; LINKER includes 3-100 atoms; and OLIGO has a structure of the following formula:

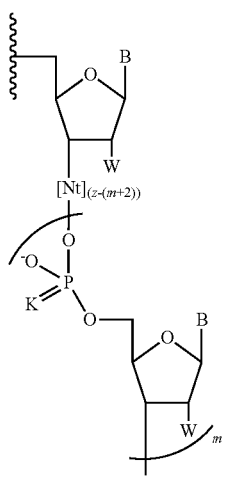

-continued

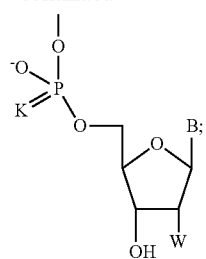

where B is a nucleobase; K is S or O; m is 0 or 1; z is an integer of 3 to about 100; W is OH, F, OMe, or H; and Nt is a moiety having a formula:

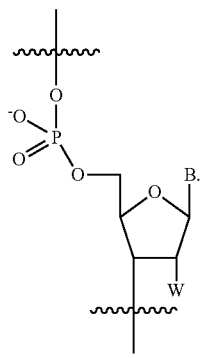

In yet other embodiments, a chemically-enhanced primer has a structure of the formula: $(Cn)_x$-OLIGO, wherein $(Cn)_x$ has a structure of the following formula:

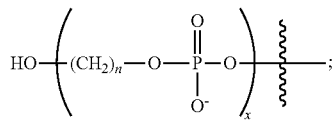

where each instance of n is independently an integer of 1 to 9; and x is an integer of 1 to about 30; and OLIGO has a structure as defined for Formula IV.

In further embodiments of the chemically-enhanced primer of Formula IV, a chemically-enhanced primer is provided having a structure of the following formula: $(Cn)_x$-OLIGO*, wherein $(Cn)_x$ has a structure of the following formula:

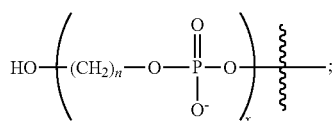

where each instance of n is independently an integer of 1 to 9; and x is an integer of 1 to about 30; and OLIGO* has a structure of the following formula:

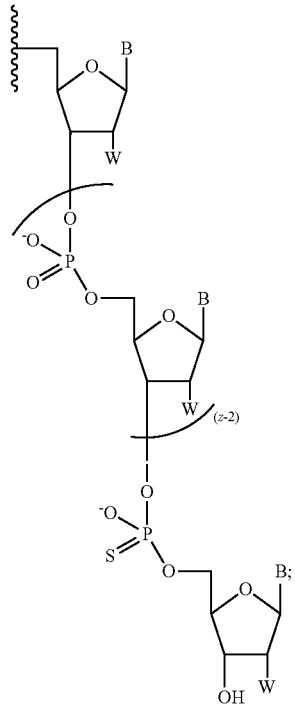

where B is a nucleobase; W is OH, F, OMe, or H; x is an integer of 1 to about 30; and z is an integer of 3 to about 100.

In some embodiments of the chemically-enhanced primer of Formula IV, the chemically-enhanced primer is fluorescently labeled. In other embodiments, the chemically-enhanced primer is not fluorescently labeled. The chemically-enhanced primer may have an OLIGO portion where W is H or OH. The chemically-enhanced primer may have K=S. In other embodiments, the chemically-enhanced primer may have K=O. In some embodiments of the chemically-enhanced primer, n is 3 or 6. In other embodiments, each instance of n is independently 3 or 6. In yet other embodiments, when x is greater than 5, then a first plurality of n is selected to be 3, and a second plurality of n is selected to be 6. For some embodiments of the chemically-enhanced primer, x is 5, 8, 9, 10, or 15. The chemically-enhanced primer may have z, where z is an integer of 5 to 30.

For some embodiments of the chemically-enhanced primer of Formula IV, OLIGO may be a universal primer. In some embodiments, the universal primer is selected from M13, US1, T7, SP6, and T3. In other embodiments of the chemically-enhanced primer of Formula IV, OLIGO may be a gene specific oligonucleotide sequence.

For some embodiments of the chemically-enhanced primer of Formula IV, the chemically-enhanced primer is resistant to digestion by a nuclease. In some embodiments, the nuclease is selected from exonuclease I, Exo III, Pfu and DNA pol I.

In another aspect, the invention provides a chemically-enhanced primer having a structure of Formula I:

Formula I

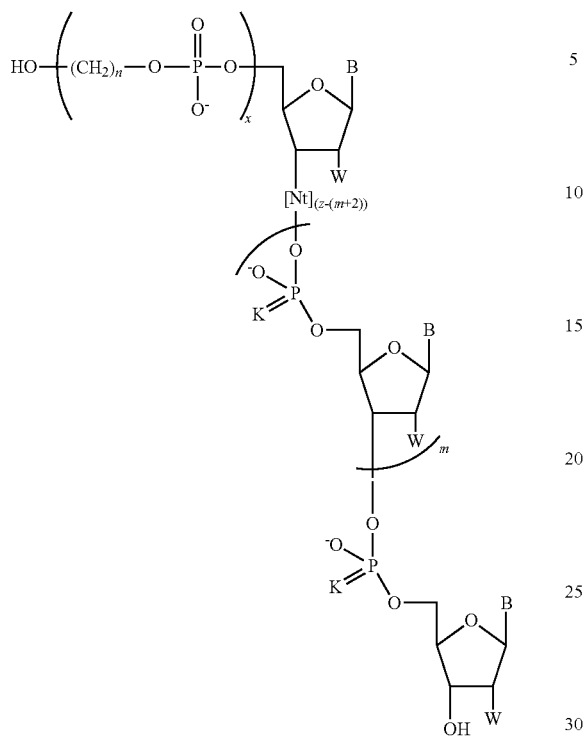

where B is a nucleobase; K is S or O; each instance of n is independently an integer of 1 to 9; m is 0 or 1; x is an integer of 1 to about 30; z is an integer of 3 to about 100; and Nt is a moiety having a formula:

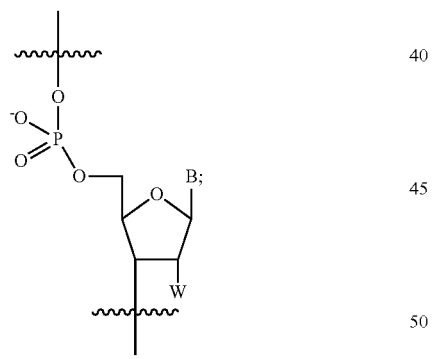

and W is OH, F, OMe, or H.

In some embodiments of the chemically-enhanced primer of Formula I, m is 0. In other embodiments, K is S. For yet other embodiments, K is O. The chemically-enhanced primer may be fluorescently labeled. In other embodiments, the chemically-enhanced primer is not fluorescently labeled. The chemically-enhanced primer may have a structure where W is H or OH.

In some embodiments of the chemically-enhanced primer of Formula I, n is 3 or 6. In other embodiments, when x is greater than 5, a first plurality of n is selected to be 3, and a second plurality of n is selected to be 6. In yet other embodiments, x is 5, 8, 9, 10, or 15. In some embodiments, z is an integer of 5 to 30.

In some embodiments of the chemically-enhanced primer of Formula I, having OLIGO representing the oligonucleotide portion of the primer, OLIGO may be a universal primer. In some embodiments, the universal primer is selected from M13, US1, T7, SP6, and T3. In other embodiments, having OLIGO representing the oligonucleotide portion of the primer, OLIGO may be a gene specific oligonucleotide sequence In some embodiments of the chemically-enhanced primer of Formula I, has a structure of one of the following formulae:

Formula 1-A

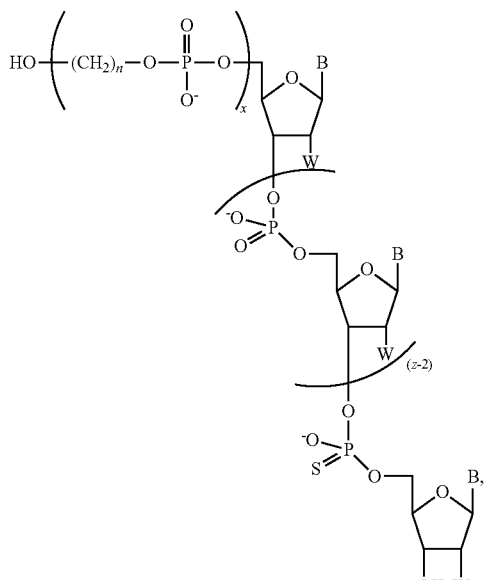

Formula I-B

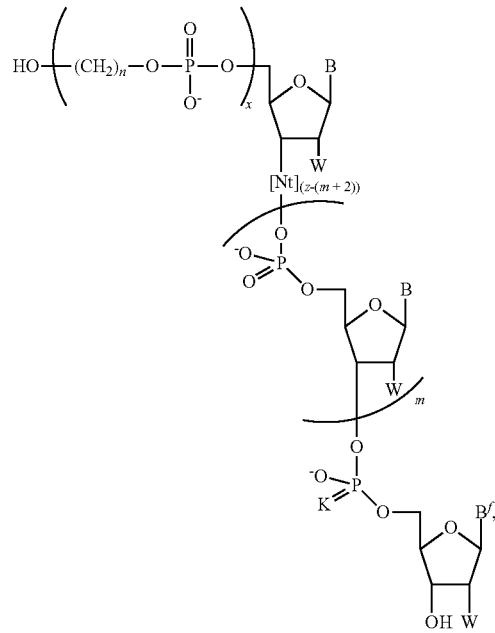

Formula I-C
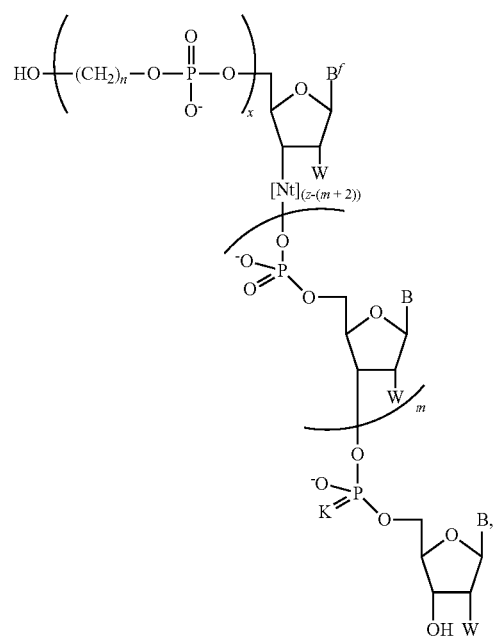
Formula I-D
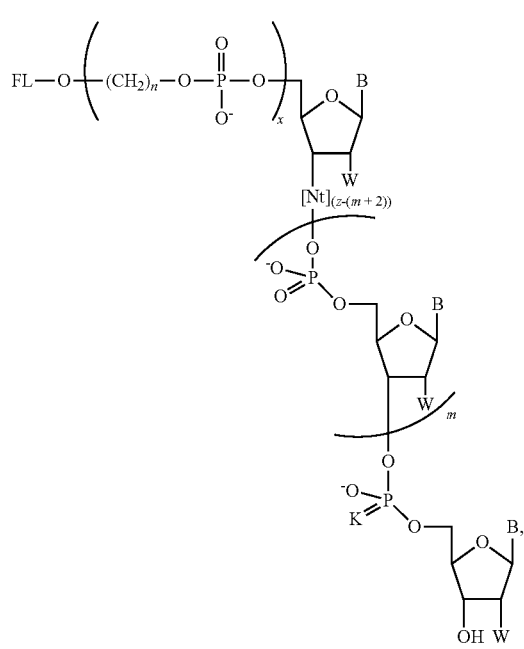
Formula I-E
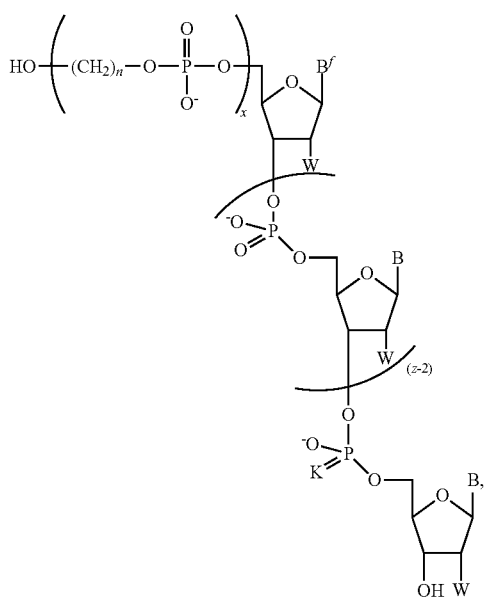
Formula I-F Formula I-G
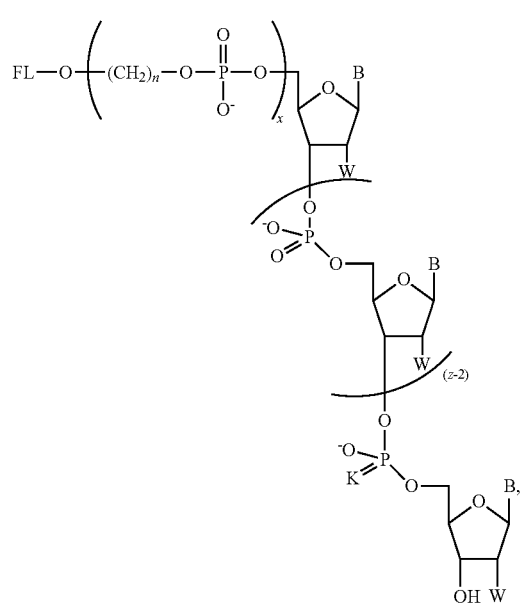
Formula I-H
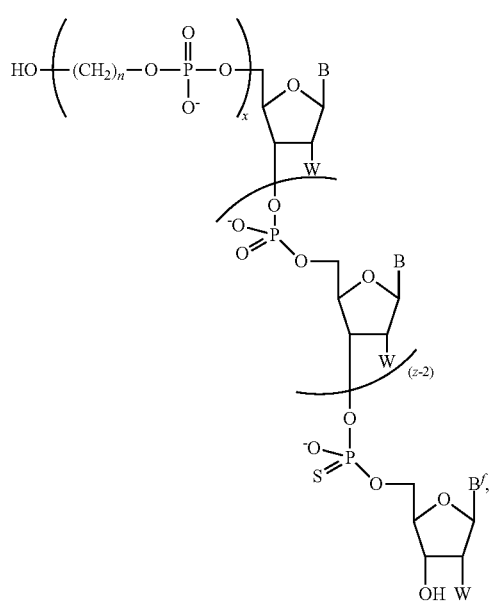
Formula I-J
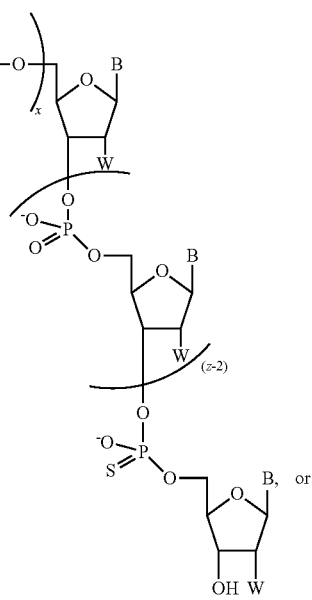
Formula I-K
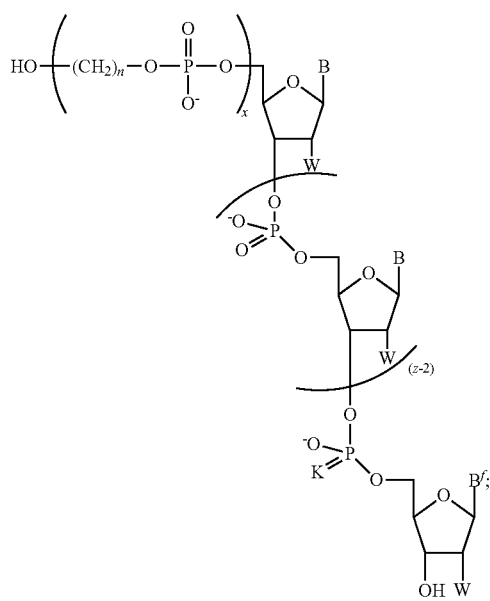
wherein FL is a dye label and B' is a dye labeled nucleobase.
In another aspect, a composition is provided for sequencing nucleic acid comprising: a chemically-enhanced primer of Formula I:

Formula I

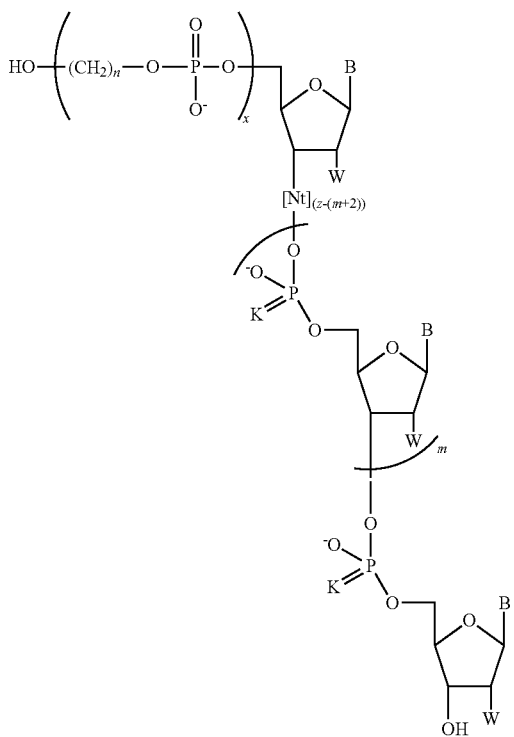

wherein B is a nucleobase; K is S or O; each n is independently an integer of 1 to 9; m is 0 or 1; x is an integer of 1 to about 30; z is an integer of 3 to about 100; W is OH, F, OMe, or H; and Nt is a moiety having a formula:

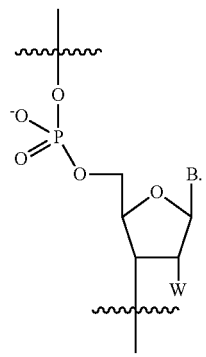

In some of the embodiments of the composition for sequencing nucleic acid, the chemically-enhanced primer of Formula I has a structure having a formula of one of Formula I-A, Formula I-B, Formula I-C, Formula I-D, Formula I-E, Formula I-F, Formula I-G, Formula I-H, Formula I-J, or Formula I-K.

In some of the embodiments of the composition for sequencing nucleic acid, the oligonucleotide sequence portion of the chemically-enhanced primer may be a universal primer. In some embodiments, the universal primer is selected from M13, US1, T7, SP6, and T3. In further embodiments, the universal primer is M13. In some embodiments, the chemically-enhanced primer may include one nuclease-resistant linkage.

In some of the embodiments of the composition for sequencing nucleic acid, the composition further includes a polymerase, a nuclease, deoxynucleotide triphosphates, dideoxynucleotide triphosphates and a dye-label. In other embodiments, the composition further includes a polymerase, deoxynucleotide triphosphates, dideoxynucleotide triphosphates and a dye-label. In some embodiments, the dideoxynucleotide triphosphates may comprise dye-labeled dideoxynucleotide triphosphates. The dye-labeled dideoxynucleotide triphosphates may comprise fluorescent dye-labeled dideoxynucleotide triphosphates. In other embodiments, the dye-label is attached to the NCM or the oligonucleotide sequence.

In some of the embodiments of the composition for sequencing nucleic acid, when a nuclease is present, the nuclease is selected from exonuclease I, Exo III, Pfu and DNA pol I. The composition for sequencing nucleic acid may further comprise a PCR amplification reaction product that includes non-nuclease-resistant amplification primer(s). The PCR amplification reaction product may further comprise an amplified DNA target sequence.

In another aspect, a method is provided to prepare DNA for sequencing, comprising the steps of: amplifying the DNA under conditions to produce amplification reaction products, the amplification reaction products comprising excess amplification primer; and contacting the amplification reaction products with a reaction mixture comprising a nuclease and a chemically-enhanced primer, whereby the excess amplification primer is degraded by the nuclease and the chemically-enhanced primer is essentially non-degraded, wherein the chemically-enhanced primer includes at least one negatively charged moiety (NCM) and an oligonucleotide sequence having a) non-nuclease resistant inter-nucleotide linkages or b) at least one nuclease resistance inter-nucleotide linkage.

In some of the embodiments of the method for preparing DNA for sequencing, the amplification reaction products further comprise a target amplicon. In some of the embodiments of the method for preparing DNA for sequencing, the chemically-enhanced primer includes one nuclease-resistant linkage at a terminal 3' end of the primer. In other embodiments, the NCM includes one or more negatively charged moieties either at a terminal 5' end.

In another aspect, a method is provided to sequence DNA, comprising the steps of: reacting DNA in a sequencing reaction wherein the chemically-enhanced primer primes the sequencing reaction.

In another aspect, a method is provided to sequence DNA, comprising the steps of: amplifying DNA in a first reaction mixture comprising nuclease-sensitive amplification primers to form amplified DNA; contacting the first reaction mixture of the amplifying step with a second reaction mixture comprising a nuclease and a chemically-enhanced primer whereby the nuclease sensitive amplification primers are degraded by the nuclease; inactivating the nuclease; and reacting the amplified DNA in a sequencing reaction wherein the chemically-enhanced primer primes the sequencing reaction.

In some of the embodiments of the methods for sequencing DNA, the method further includes the steps of: obtaining sequencing results based on the sequencing reaction; and determining a nucleotide base sequence of the amplified DNA based on the results. In other embodiments, the step of amplifying DNA includes the step of polymerase chain reaction amplification. In yet other embodiments, the sequencing reaction includes cycle sequencing. In some embodiments, the nuclease is selected from exonuclease I, Exo III, Pfu and DNA pol I.

In some of the embodiments of the methods for sequencing DNA, the second reaction mixture further includes a polymerase, deoxynucleotide triphosphates, dideoxynucleotide triphosphates and a dye-label.

In some of the embodiments of the methods for sequencing DNA, the chemically-enhanced primer includes an oligonucleotide sequence having a) non-nuclease resistant inter-nucleotide linkages or b) at least one nuclease resistance inter-nucleotide linkage and a NCM. In some embodiments, the NCM includes a moiety having a structure of the following formula:

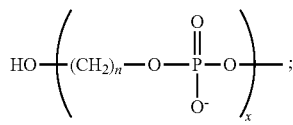

wherein each n is independently an integer of 1 to 9, and x is an integer of 1 to about 30. In some embodiments, the chemically-enhanced primer has a structure of one of Formula I, Formula I-A, Formula I-B, Formula I-C, Formula I-D, Formula I-E, Formula I-F, Formula I-G, Formula I-H, Formula I-J, Formula I-K, Formula II, Formula III, Formula IV, $(Cn)_x$-OLIGO, $(Cn)_x$-OLIGO*, Formula V, Formula V-A, Formula VI, Formula VI-A, or Formula VI-A1, as disclosed here.

In some of the embodiments of the methods for sequencing DNA, the chemically-enhanced primer includes one nuclease-resistant linkage at a terminal 3' end. In other embodiments, the chemically-enhanced primer includes a plurality of NCMs either at a terminal 5' end or within a oligonucleotide sequence of the chemically-enhanced primer. In some other embodiments, the NCM includes a plurality of (Cn) spacers. In other embodiments, n equals 3, the NCM includes a $(C3)_x$ spacer, wherein x equals at least 5, at least 6, at least 8, at least 9, at least 10, at least 15 at least 18, at least 20, at least 24 or more C3 spacers in a linear or branched arrangement. In other embodiments, the plurality of (Cn) spacers may be doubler or a trebler.

In yet another aspect, a method is provided to resolve sequencing ambiguity comprising the steps of: amplifying DNA suspected of comprising an ambiguity in a first reaction mixture comprising nuclease-sensitive amplification primers to form amplified DNA; contacting the first reaction mixture of the amplifying step with a second reaction mixture comprising a nuclease and a chemically-enhanced primer, whereby the nuclease sensitive amplification primers are degraded by the nuclease; inactivating the nuclease; and reacting the amplified DNA in a sequencing reaction wherein the chemically-enhanced primer primes the sequencing reaction. In some embodiments, wherein the DNA is an HLA gene, an HLA allele, an oncogene or a sequence comprising a polymorphism.

In a further aspect, a system is provided to sequence DNA comprising: amplifying DNA in a first reaction mixture comprising nuclease sensitive amplification primers to form amplified DNA; contacting the first reaction mixture of the amplifying step with a second reaction mixture comprising a nuclease and a chemically-enhanced primer, whereby the nuclease sensitive amplification primers are degraded by the nuclease; inactivating the nuclease; reacting the amplified DNA in a sequencing reaction wherein the chemically-enhanced primer primes said sequencing reaction; and identifying a nucleotide base sequence of the amplified DNA by mobility-dependent separation of sequencing reaction products.

In some embodiments of the system for sequencing DNA, the mobility-dependent separation is selected from separation by charge and separation by size. In some embodiments, the separation by size plus charge is selected from gel electrophoresis and capillary electrophoresis. In other embodiments, the separation by size is selected from a liquid gradient and a denaturing gradient.

In yet a further aspect, a kit is provided including a chemically-enhanced primer. In some embodiments, the chemically-enhanced primer includes a NCM and an oligonucleotide sequence having a) non-nuclease resistant inter-nucleotide linkages or b) at least one nuclease resistance inter-nucleotide linkage. In other embodiments, the NCM includes a moiety having a structure of the following formula

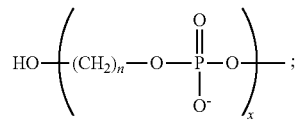

where each n is independently an integer of 1 to 9, and x is an integer of 1 to about 30. In some embodiments, the chemically-enhanced primer of the kit has a structure of one of Formula I, Formula I-A, Formula I-B, Formula I-C, Formula I-D, Formula I-E, Formula I-F, Formula I-G, Formula I-H, Formula I-J, Formula I-K, Formula II, Formula III, Formula IV, $(Cn)_x$-OLIGO, $(Cn)_x$-OLIGO*, Formula V, Formula V-A, Formula VI, Formula VI-A, or Formula VI-A1, as disclosed here. In some embodiments, the chemically enhanced primer has an oligonucleotide sequence selected from the group consisting of $Cn)_x$-US1, $(Cn)_x$-M13-forward, $(Cn)_x$-M13-reverse, $(Cn)_x$-T7, $(Cn)_x$-SP6, and $(Cn)_x$-T3. In some embodiments, the chemically enhanced primer the chemically-enhanced primer is $(Cn)_x$-GSO, wherein GSO is a gene specific oligonucleotide sequence, and includes 50 or fewer nucleotides.

In some embodiments of the kit, the kit further includes at least one of instructions for use, a nuclease, a sufficient quantity of enzyme for a sequencing reaction or a fragment analysis reaction, buffer to facilitate the sequencing reaction or fragment analysis reaction, dNTPs, modified dNTPs, dNTP analogs and 7-Deaza-dGTP for strand extension during sequencing reaction or fragment analysis reaction, ddNTPs, a dye-label, loading solution for preparation of the sequenced material or fragment analysis material for electrophoresis, genomic DNA as a template control, a size marker to insure that materials migrate as anticipated in the separation medium, and a protocol and manual to educate the user and limit error in use. In other embodiments, the kit further includes at least one of instructions for use, a sufficient quantity of enzyme for a sequencing reaction or a fragment analysis reaction, buffer to facilitate the sequencing reaction or fragment analysis reaction, dNTPs, modified dNTPs, dNTP analogs and 7-Deaza-dGTP for strand extension during sequencing reaction or fragment analysis reaction, ddNTPs, a dye-label, loading solution for preparation of the sequenced material or fragment analysis material for electrophoresis, genomic DNA as a template control, a size marker to insure that materials migrate as anticipated in the separation medium, and a protocol and manual to educate the user and limit error in use. In other embodiments, According to various embodiments, the present teachings provide a composition for a chemically-enhanced primer. According to various embodiments, the primer can comprise a negatively charged moiety, an oligonucleotide sequence and a nuclease-resistant linkage. In various embodiments the primer can be used in fragment analysis, sequencing nucleic acid and for improving resolution, PCR through sequencing workflows with POP-7™ polymer on capillary electrophoresis instruments such as those manufactured by Applied Biosystems (Foster City, Calif.).

According to various embodiments, the present teachings provide a composition for sequencing nucleic acid. According to various embodiments, the composition can comprise a composition comprising a chemically-enhanced primer comprising an oligonucleotide sequence, a negatively charged moiety (NCM) and at least one nuclease-resistant linkage. In various embodiments the composition can further comprise a polymerase, a nuclease, deoxynucleotide triphosphates (dNTPs), and dideoxynucleotide triphosphates (ddNTPs) and at least one dye-label. In various embodiments of the method, the composition can be added in one step directly to a PCR reaction product, without first removing excess PCR amplification primers from the PCR reaction product.

According to various embodiments, the present teachings relate to a method of preparing DNA for sequencing, a method of sequencing DNA, and a composition for sequencing DNA. The teachings provide a method of PCR/sequencing (including cycle sequencing) that can be quicker and simpler, and require fewer steps, than traditional methods. The methods of the present teachings utilize a chemically-enhanced primer in combination with nuclease, which can reduce sequence noise and remove undesired sequence priming. The present teachings further provide a composition for DNA sequencing that can be used with such a method.

According to various embodiments, the present teachings disclose a method of preparing DNA for sequencing. In some embodiments, the DNA preparation method can eliminate at least one reagent addition step used in conventional PCR/cycle sequencing, thereby reducing the number of processing steps.

According to various embodiments, a method of preparing DNA for sequencing is provided that can comprise amplifying DNA under conditions to produce amplification reaction products, the amplification reaction products comprise excess amplification primer, and contacting the amplification reaction products with a reaction mixture comprising a nuclease and a chemically-enhanced sequencing primer, under conditions in which the excess amplification primer is degraded by the nuclease. According to various embodiments, the chemically-enhanced primer is essentially non-degraded under such conditions. In some embodiments, the excess amplification primer can comprise inter-nucleotide phosphodiester bonds that are susceptible to nuclease cleavage. In some embodiments the chemically-enhanced primer can comprise at least one inter-nucleotide nuclease-resistant linkage, including but not limited to at least one phosphorothioate bond that is not susceptible to nuclease cleavage.

The present teachings further provide a method of sequencing DNA that can generate clean, clear and accurate sequencing data by a simpler workflow compared to conventional methods, and that requires less time. According to various embodiments, a DNA sequencing method is provided that can comprise adding a sequencing reaction mix directly to a completed PCR amplification reaction, without first performing a separate cleanup step; that is, without first removing excess PCR amplification primers by the addition of a nuclease and completing a nuclease inactivation step, followed by a second addition of sequencing primers and reagents.

According to various embodiments, a method of sequencing DNA is provided that can comprise amplifying DNA in a first reaction mixture comprising nuclease-sensitive amplification primers to form amplified DNA, contacting the first reaction mixture with a second reaction mixture comprising a nuclease and a chemically-enhanced primer under conditions in which the nuclease-sensitive amplification primers are degraded by the nuclease, inactivating the nuclease, and causing the amplified DNA to serve as template in a sequencing reaction under conditions in which the chemically-enhanced primer primes the sequencing reaction.

The present teachings further provide a system for sequencing DNA that can comprise amplifying DNA in a first reaction mixture comprising nuclease sensitive amplification primers to form amplified DNA, contacting said first reaction mixture of the amplifying step with a second reaction mixture comprising a nuclease and a chemically-enhanced primer, under conditions in which the nuclease sensitive amplification primers are degraded by the nuclease; inactivating the nuclease and causing the amplified DNA to react in a sequencing reaction under conditions in which the chemically-enhanced primer primes said sequencing reaction; and identifying a nucleotide base sequence of the amplified DNA by mobility-dependent separation of sequencing reaction products.

The present teachings further provide a kit. In various embodiments the kit comprises a chemically-enhanced primer comprising a negatively charged group, an oligonucleotide sequence and a nuclease resistant moiety. In further embodiments, the kit can have at least one of a instructions for use, a nuclease, a sufficient quantity of enzyme for sequencing or fragment analysis, buffer to facilitate the sequencing or fragment analysis, dNTPs, modified dNTPs, dNTP analogs and 7-Deaza-dGTP for strand extension during sequencing or fragment analysis, ddNTPs, a dye-label, loading solution for preparation of the sequenced or fragment analyzed material for electrophoresis, genomic DNA as a template control, a size marker to insure that materials migrate as anticipated in the separation medium, and a protocol and manual to educate the user and limit error in use.

Various patents, patent applications, and other publications are referred to herein, all of which are incorporated herein in their entireties by reference. In addition, the following standard reference works are incorporated herein by reference: Current Protocols in Molecular Biology, John Wiley & Sons, N.Y., edition as of October 2007; Sambrook, Russell, and Sambrook, Molecular Cloning: A Laboratory Manual, 3rd ed., Cold Spring Harbor Laboratory Press, Cold Spring Harbor, 2001. In the event of a conflict between the instant specification and any document incorporated by reference, the specification shall control, it being understood that the determination of whether a conflict or inconsistency exists is within the discretion of the inventors and can be made at any time.

Additional features and advantages of the present teachings will be evident from the description that follows, and in part will be apparent from the description, or can be learned by practice of the present teachings. It is to be understood that both the foregoing summary and the following detailed description are exemplary and explanatory only and are intended to provide further explanation of the present teachings without limiting the present teachings.

BRIEF DESCRIPTION OF THE DRAWINGS

The accompanying drawings, which are incorporated in and constitute a part of this specification exemplify embodiments disclosed and, together with the description, serve to explain and illustrate principles of disclosed embodiments. Specifically:

FIG. 1 is a diagrammatic representation of a standard PCR/cycle sequencing workflow; with five steps in FIG. 1A and four steps in FIG. 1B, the disclosed improved workflow. The numbers indicated in each box represents the number of minutes each step requires. It is shown that use of the chemically-enhanced primers permit significant reduction in workflow time.

DETAILED DESCRIPTION

To facilitate understanding of the present teachings, the following definitions are provided. It is to be understood that, in general, terms not otherwise defined are to be given their ordinary meanings or meanings as generally accepted in the art.

As used herein, the term "PCR/cycle sequencing" refers to a method for determining a nucleotide sequence of DNA by PCR amplifying the DNA, followed by sequencing reactions repeated (or cycled) several times. This cycling is similar to PCR because the sequencing reaction is allowed to proceed at 42° C.-55° C., then stopped at 95° C., and started again at 42° C.-55° C., and uses a thermostable DNA polymerase.

Figure 2:
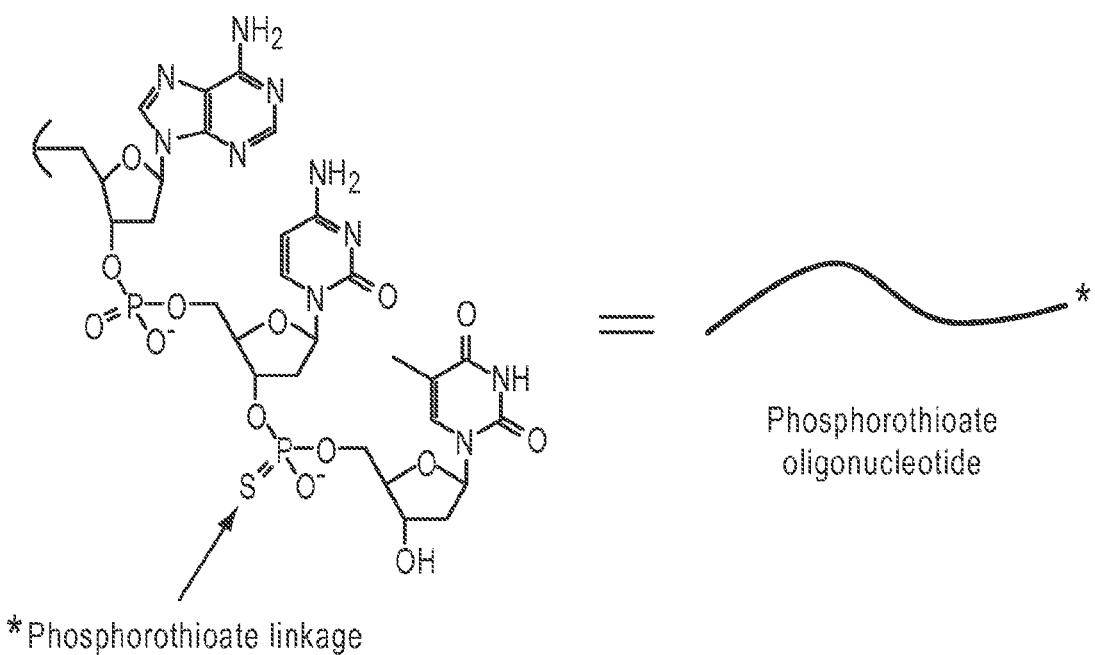
FIG. 2 illustrates an exonuclease I-resistant oligonucleotide having a nuclease-resistant linkage at the terminal 3' end, according to various embodiments.

As used herein, the term "phosphorothioate linkage" refers to an inter-nucleotide linkage comprising a sulfur atom in place of a non-bridging oxygen atom within the phosphate linkages of a sugar phosphate backbone. The term phosphorothioate linkage refers to both phosphorothioate inter-nucleotide linkages and phosphorodithioate inter-nucleotide linkages. A "phosphorothioate linkage at a terminal 3' end" refers to a phosphorothioate linkage at the 3' terminus, that is, the last phosphate linkage of the sugar phosphate backbone at the 3' terminus. A phosphorothioate linkage at a terminal 3' end is illustrated in FIG. 2.

As used herein, the term "phosphodiester linkage" may refer to the linkage —$PO_4$— which is used to link nucleotide monomers, such as the inter-nucleotide linkages found in naturally-occurring DNA. Additionally, "phosphodiester linkage" may refer to portions of the NCMs or NCM linkers of the chemically-enhanced primers of the present disclosure.

As used herein, the term "nuclease-resistant linkage" refers to an oligonucleotide sequence, such as a primer, that is resistant to digestion in the 3' to 5' direction by nuclease. Phosphorothioate and boronophosphate linkages are two examples of nuclease-resistant linkages. The examples are not to be construed as limited to just these examples.

As used herein, the term "primer" refers to an oligonucleotide, typically between about 10 to 100 nucleotides in length, capable of selectively binding to a specified target nucleic acid or "template" by hybridizing with the template. The primer can provide a point of initiation for template-directed synthesis of a polynucleotide complementary to the template, which can take place in the presence of appropriate enzyme(s), cofactors, substrates such as nucleotides and oligonucleotides and the like.

As used herein, the term "chemically-enhanced primer" refers to a primer that can have a negatively charged moiety at a terminal 5' end of the primer or within the primer. The primer can also include a nuclease-resistant linkage at the last phosphate linkage of the sugar phosphate backbone at the 3' terminus.

As used herein, the term "sequencing primer" refers to an oligonucleotide primer that is used to initiate a sequencing reaction performed on a nucleic acid. The term "sequencing primer" refers to both a forward sequencing primer and to a reverse sequencing primer.

As used herein, the term "extension primer" refers to an oligonucleotide, capable of annealing to a nucleic acid region adjacent a target sequence, and serving as an initiation primer for elongation of the oligonucleotide by using the target sequence as the complementary template for nucleotide extension under suitable conditions well known in the art. Typically, a sequencing reaction employs at least one extension primer or a pair of extension primers. The pair would include an "upstream" or "forward" primer and a "downstream" or "reverse" primer, which delimit a region of the nucleic acid target sequence to be sequenced.

As used herein, the term "amplification primer" refers to an oligonucleotide, capable of annealing to an RNA or DNA region adjacent a target sequence, and serving as an initiation primer for nucleic acid synthesis under suitable conditions well known in the art. Typically, a PCR reaction employs a pair of amplification primers including an "upstream" or "forward" primer and a "downstream" or "reverse" primer, which delimit a region of the RNA or DNA to be amplified.

As used herein, the term "tailed primer" or "tailed amplification primer" refers to a primer that includes at its 3' end a sequence capable of annealing to an RNA or DNA region adjacent a target sequence, and serving as an initiation primer for DNA synthesis under suitable conditions well known in the art. The primer includes its 5' end a sequence capable of annealing to a sequencing primer, for example, an oligonucleotide sequence, an universal sequencing primer, a gene-specific primer, primer and the like.

As used herein, the term "amplifying" refers to a process whereby a portion of a nucleic acid is replicated. Unless specifically stated, "amplifying" refers to a single replication or to an arithmetic, logarithmic, or exponential amplification.

As used herein, the term "target amplicon" refers to an amplification product having the target sequence of interest and resulting form an amplification reaction, e.g., a polymerase chain reaction (PCR).

As used herein, the terms "extend", "extension" and "extending" are used interchangeably and refer to a process whereby an oligonucleotide is increased in length at the 3' end according to a template target nucleic acid sequence. Unless specifically stated, "extend" refers to a single expansion or to a plurality of parallel or multiple expansions of a target or multiple target nucleic acid target sequences.

As used herein, the term "determining a nucleotide base sequence" or the term "determining information about a sequence" encompasses "sequence determination" and also encompasses other levels of information such as eliminating one or more possibilities for a sequence. It is noted that performing sequence determination of a polynucleotide typically yields equivalent information regarding the sequence of a perfectly complementary (100% complementary) polynucleotide and thus is equivalent to sequence determination performed directly on a perfectly complementary polynucleotide.

The term "nucleic acid sequence" as used herein can refer to the nucleic acid material itself and is not restricted to the sequence information (i.e. the succession of letters chosen among the five base letters A, C, G, T, or U) that biochemically characterizes a specific nucleic acid, for example, a DNA or RNA molecule. Nucleic acids shown herein are presented in a 5'→3' orientation unless otherwise indicated.

The term "mobility-dependent separation" as used herein can refer to the separation of nucleic acid fragments due to the charge and size associated with the fragment.

The term "fluorescent dye" as used herein refers to moieties that absorb light energy at a defined excitation wavelength and emit light energy at a different wavelength. Preferably the fluorescent dyes selected for use are spectrally resolvable. As used herein, "spectrally resolvable" means that the dyes can be distinguished on the basis of their spectral characteristics, particularly fluorescence emission wavelength, under conditions of operation. For example, the identity of the one or more terminal nucleotides can be correlated to a distinct wavelength of maximum light emission intensity, or perhaps a ratio of intensities at different wavelengths.

The term "nucleobase" or "base" as used herein refers to a nitrogen-containing heterocyclic moiety capable of forming Watson-Crick type hydrogen bonds with a complementary nucleobase or nucleobase analog, e.g. a purine, a 7-deazapurine, or a pyrimidine. Typical nucleobases are the naturally occurring nucleobases adenine, guanine, cytosine, 5mC, uracil, thymine, and analogs of naturally occurring nucleobases, e.g. 7-deazaadenine, 7-deaza-8-azaadenine, 7-deazaguanine, 7-deaza-8-azaguanine, N6-Δ2 isopentenyl-adenine (6iA), N6-Δ2-isopentenyl-2-methylthioadenine (2 ms6iA), N2-dimethyl-guanine (dmG), 7-methylguanine (7mG), inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 2-thiopyrimidine, 6-thioguanine, 4-thiothymine, 4-thiouracil, 6-methylguanine, $N^6$-methyl-adenine, $O^4$-methylthymine, 5,6-dihydrothymine, 5,6-dihydrouracil, 4-methylindole, pyrazolo[3,4-D]pyrimidines (see, e.g., U.S. Pat. Nos. 6,143,877 and 6,127,121 and PCT Published Application WO 01/38584) and ethenoadenine. Nonlimiting examples of nucleotide bases can be found, e.g., in Fasman, Practical Handbook of Biochemistry and Molecular Biology, pp. 385-394, CRC Press, Boca Raton, Fla. (1989).

As used herein, the terms "polynucleotide", "nucleic acid", or "oligonucleotide" refers to a linear polymer of nucleosides (including deoxyribonucleosides, ribonucleosides, or analogs thereof) joined by inter-nucleosidic linkages. Whenever a polynucleotide such as an oligonucleotide is represented by a sequence of letters, such as "ATGC-CTG," it will be understood that the nucleotides are in 5'→3' order from left to right and that "A" denotes deoxyadenosine, "C" denotes deoxycytidine, "G" denotes deoxyguanosine, and "T" denotes deoxythymidine, unless otherwise noted. The letters A, C, G, and T can be used to refer to the bases themselves, to nucleosides, or to nucleotides comprising the bases, as is standard in the art. In naturally occurring polynucleotides, the inter-nucleoside linkage is typically a phosphodiester bond, and the subunits are referred to as "nucleotides." Oligonucleotide primers comprising other inter-nucleoside linkages, such as phosphorothioate linkages, are used in certain embodiments of the teachings. It will be appreciated that one or more of the subunits that make up such an oligonucleotide primer with a non-phosphodiester linkage can not comprise a phosphate group. Such analogs of nucleotides are considered to fall within the scope of the term "nucleotide" as used herein, and nucleic acids comprising one or more inter-nucleoside linkages that are not phosphodiester linkages are still referred to as "polynucleotides", "oligonucleotides", etc.

As used herein "sequence determination", "determining a nucleotide base sequence", "sequencing", and like terms includes determination of partial as well as full sequence information. That is, the term includes sequence comparisons, fingerprinting, and like levels of information about a target polynucleotide, as well as the express identification and ordering of each nucleoside of the target polynucleotide within a region of interest. In certain embodiments, "sequence determination" comprises identifying a single nucleotide, while in other embodiments more than one nucleotide is identified. Identification of nucleosides, nucleotides, and/or bases are considered equivalent herein. It is noted that performing sequence determination on a polynucleotide typically yields equivalent information regarding the sequence of a perfectly complementary polynucleotide and thus is equivalent to sequence determination performed directly on a perfectly complementary polynucleotide.

As used herein, the term "kit" refers to any delivery system for delivering materials. In the context of reaction assays, such delivery systems include systems that allow for the storage, transport, or delivery of reaction reagents (e.g., oligonucleotides, enzymes, primer set(s), etc. in the appropriate containers) and/or supporting materials (e.g., buffers, written instructions for performing the assay etc.) from one location to another. For example, kits can include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As will be appreciated by one of ordinary skill in the art, references to templates, oligonucleotides, primers, etc., generally mean populations or pools of nucleic acid molecules that are substantially identical within a relevant region rather than single molecules. For example, a "template" generally means a plurality of substantially identical template molecules; a "primer" generally means a plurality of substantially identical primer molecules, and the like.

Cycle sequencing involves adding to a target nucleic acid or an amplification product thereof, sequencing primer, deoxynucleotide triphosphates (dNTPs), dye-labeled chain terminating nucleotides (e.g., dideoxynucleotide triphosphates (ddNTPs-dyes)), and DNA polymerase, followed by thermal cycle sequencing. Standard cycle sequencing procedures are well established. Cycle sequencing procedures are described in more detail, for example, in U.S. Pat. No. 5,741,676, and U.S. Pat. No. 5,756,285, each herein incorporated by reference in its entirety. In certain embodiments, "cycle sequencing" comprises dNTPS, a sequencing primer (labeled or not), ddNTPs (labeled or not) and DNA polymerase as known to one of skill in the art. It is noted that a labeled sequencing primer can provide fragment analysis information and/or determination of the sequence of a target nucleic acid or amplification product thereof.

According to various embodiments of the present teachings, provided is a chemically-enhanced primer comprising an oligonucleotide sequence, a negatively charged moiety (NCM) and at least one nuclease-resistant linkage.

In some embodiments the at least one nuclease-resistant linkage includes but is not limited to at least one phosphorothioate linkage (PS) or at least one boronophosphate linkage. In other embodiments the nuclease-resistant linkage is not present in the chemically-enhanced primer. In yet other embodiments, a chemically-enhanced primer may comprise an oligonucleotide sequence, a negatively charged moiety (NCM), where the oligonucleotide inter-nucleotide linkages consist of phosphodiester inter-nucleotide linkages.

The primer can be used to prime a target nucleic acid in a sequencing reaction, herein referred to as a chemically-enhanced sequencing primer or for fragment analysis, herein referred to as a chemically-enhanced extension primer. The oligonucleotide sequence can be a universal primer or a gene specific nucleotide sequence. Examples of universal primers include but are not limited to M13 (P/N 402071 and 402072, Applied Biosystems), US1 (UNISEQ, PLoS Medicine 3(10) e431 (2006)), T7 (P/N 402126, but without dye, Applied Biosystems), SP6 (P/N 402128, but without dye, Applied Biosystems), and T3 (P/N 402127, but without dye, Applied Biosystems). See the ABI PRIMS® 377 DNA Sequence 96-Lane Upgrade User's Manual for primer sequences. The oligonucleotide sequence can also contain a dye-label such as a fluorescent label. In various embodiments of the present teachings the NCM can be located at the terminal 5' end of the oligonucleotide sequence or within the oligonucleotide sequence. Examples of NCM include but are not limited to a phosphodiester moiety having a structure of the formula

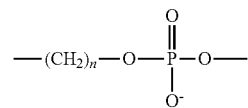

(which is introduced to the chemically-enhanced primer by reacting a phosphoramidite (available from Glen Research) with an appropriate reaction partner containing an oligonucleotide) referred to here as a (C)n spacer, wherein n can be from 1-12, the amino acids aspartic acid and glutamic acid as well as nucleotides and nucleotide analogs (dATP, dCTP, dGTP and dTTP). The NCM can contain only one negatively charged monomer or a plurality of negatively charged moieties, for example at least five, ten, 12, 15, 18, 20, 24 or more repeat units of the spacer, for example, $(Cn)_x$, where x is any integer between 1 and at least 11, at least 12, at least 15, at least 18, at least 20, at least 24 or 30 Cn spacers where "n" is 3 or 6, e.g., C3 spacers, C6 spacers or a combination of C3 and C6 spacers in a linear arrangement or a branched arrangement. The C3 and C6 spacers individually or in combination can also form a branched NCM by forming a doubler or a trebler such as, for example, $(C3)_3$-treb-M13 or $[(C3)_2$-treb]-treb-M13, where the NCM is represented by $(C3)_3$-treb or $[(C3)_2$-treb]-treb and M13 represents the oligonucleotide sequence, as would be known to one of skill in the art. The NCM can also contain a dye-label such as a fluorescent label. In various embodiments at least none, at least one, at least two or more phosphorothioate linkages can be at a terminal 3' end of the oligonucleotide sequence. The presence of at least one nuclease-resistant linkage provides resistance to digestion by 3'-5' nucleases such as Exonuclease I (P/N M0293S New England Biolabs, Ipswich, Mass.), Exo III (P/N M0206S, New England Biolabs, Ipswich, Mass.), Pfu (Promega, P/N M7741, Madison, Wis.), and DNA pol I (P/N M0209S, New England Biolabs, Ipswich, Mass.). The resistance of the chemically-enhanced primer to nuclease digestion offers the advantage of eliminating a PCR clean-up step in the PCR to sequencing protocol. Removal of the extra non-nuclease resistant amplification primers left over from the PCR step can be accomplished in the sequencing reaction mixture. A brief exposure of the PCR amplification reaction to the nuclease within the sequencing reaction mixture degrades the non-nuclease resistant amplification primers followed by an inactivation of the nuclease. The chemically-enhanced primer remains available for the sequencing reaction while the non-nuclease resistant amplification primers and the nuclease have been removed and inactivated, respectively.

In some embodiments the chemically-enhanced primer has a structure of Formula I:

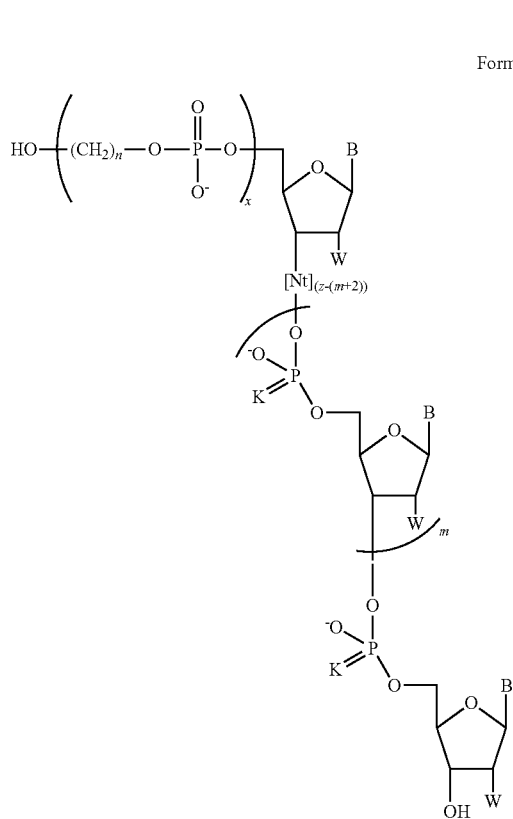

Formula I wherein B is a nucleobase; K is S or O; each n is independently an integer of 1 to 12; m is 0 or 1; x is an integer of 1 to about 50; z is an integer of 3 to about 100; W is OH, F, OMe, or H; and Nt is a moiety having a formula:

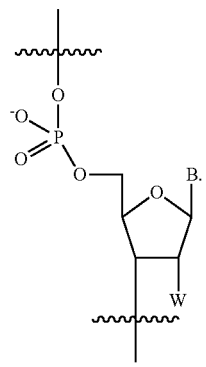

For chemically-enhanced primers having a structure of Formula I, OLIGO represents the portion of the chemically-enhanced primer of Formula I that comprises an oligonucleotide. Each nucleotide of the oligonucleotide comprises a nucleobase B portion and a ribose portion:

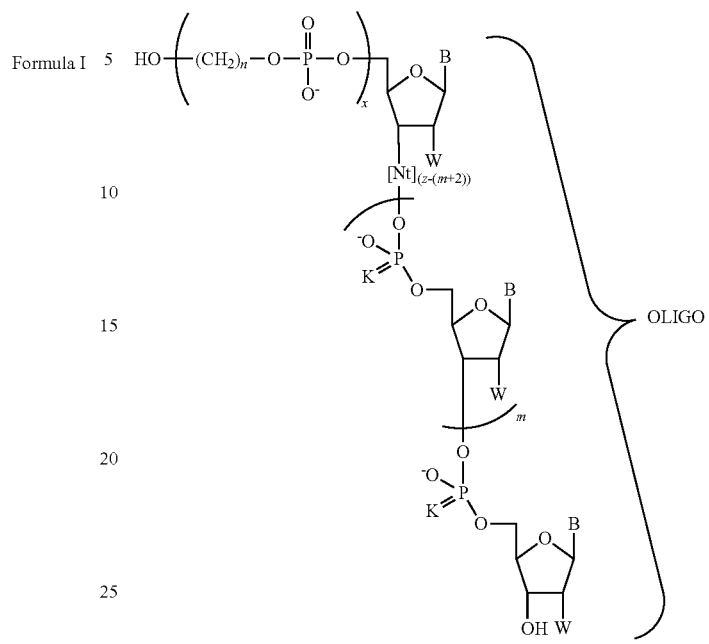

Formula I annotated

The chemically-enhanced primer of Formula I may comprise one or more B, wherein B is a naturally occurring nucleobase. In other embodiments, the chemically-enhanced primer of Formula I may comprise one or more B, wherein B is a nucleobase analog.

The chemically-enhanced primer of Formula I may have only one phosphothiorate linkage, wherein m is 0, having a structure of Formula I-A:

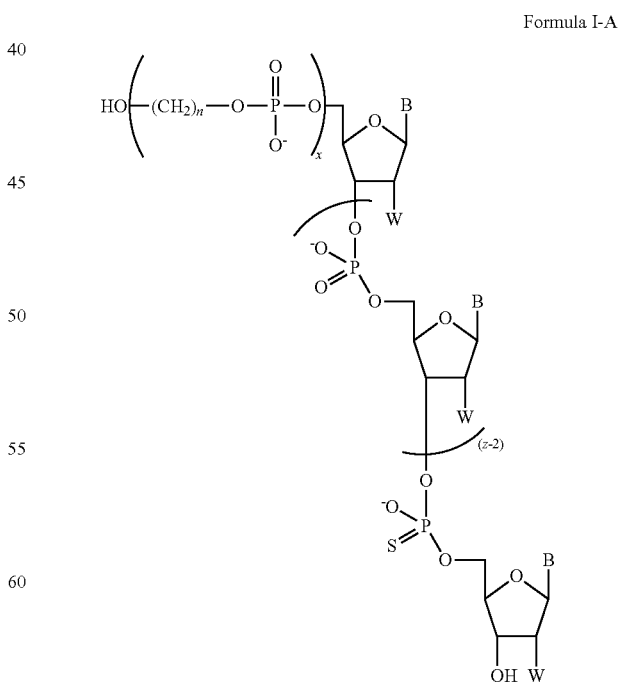

Formula I-A

The chemically-enhanced primer of Formula I may be labeled with a dye, including dyes that are fluorescent. The chemically-enhanced primer of Formula I may include one or more B labeled with a dye, and is represented as $B^f$. In some embodiments, the 3' terminal nucleotide of the chemically-enhanced primer has a fluorescently labeled B. The chemically-enhanced primer may contain a 3' fluorescently labeled terminal nucleotide wherein the B of the 3' terminal nucleotide is a nucleobase analog. Alternatively, the chemically-enhanced primer may contain a 5' terminal nucleotide having a fluorescently labeled B, which can be represented as B. In some embodiments, wherein the chemically-enhanced primer contains a 5' terminal nucleotide containing the fluorescently labeled nucleobase, $B^f$, the labeled nucleobase is a nucleobase analog. In other embodiments, the chemically-enhanced primer may contain a fluorescently labeled NCM attached directly or indirectly to one of a plurality of NCMs and/or a linker moiety to the 5' terminal nucleotide of the primer. Additionally, the chemically-enhanced primer of Formula I may be fluorescently labeled on the nucleobase of a nucleotide located at an internal position of the oligonucleotide, and the internal fluorescently labeled nucleotide may be selected to be at any position of the non-terminal portion of the oligonucleotide.

When the chemically-enhanced primer of Formula I contains a fluorescent label, the chemically-enhanced primer may have a structure of one of the following formulae:

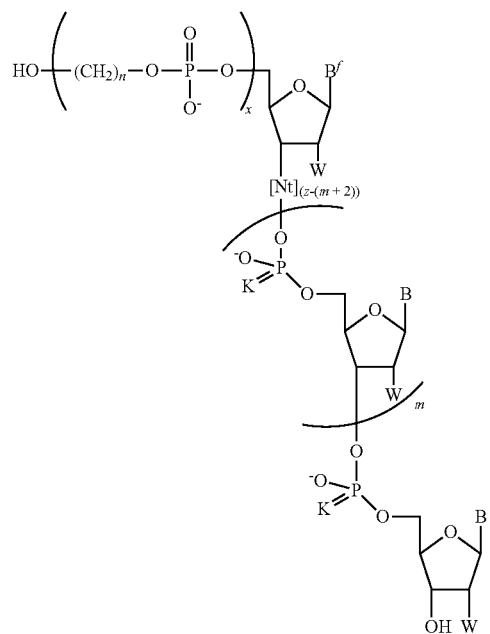

Formula I-C

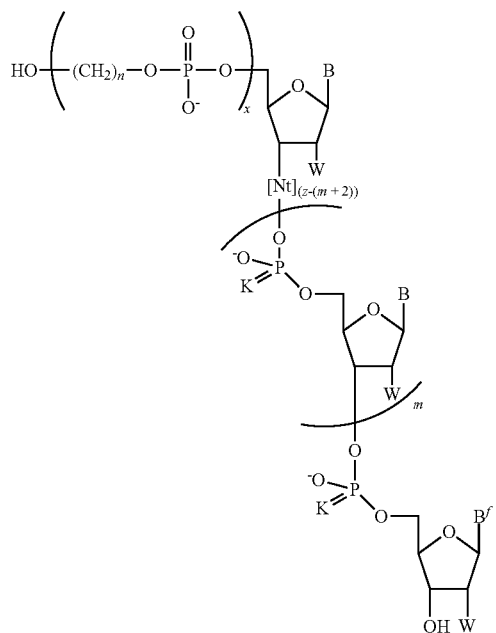

Formula I-B

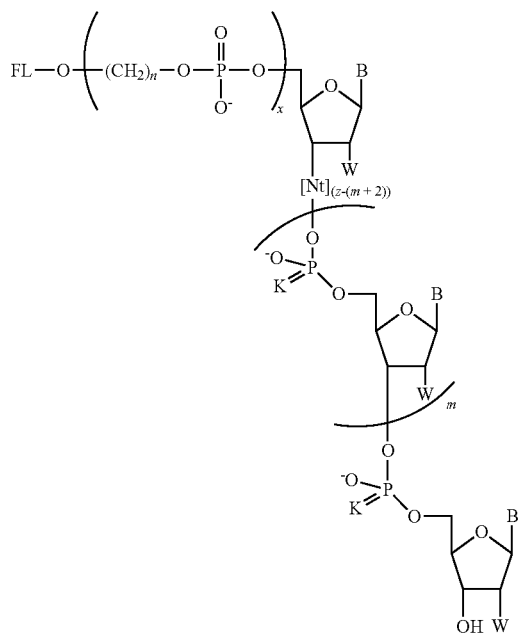

Formula I-D

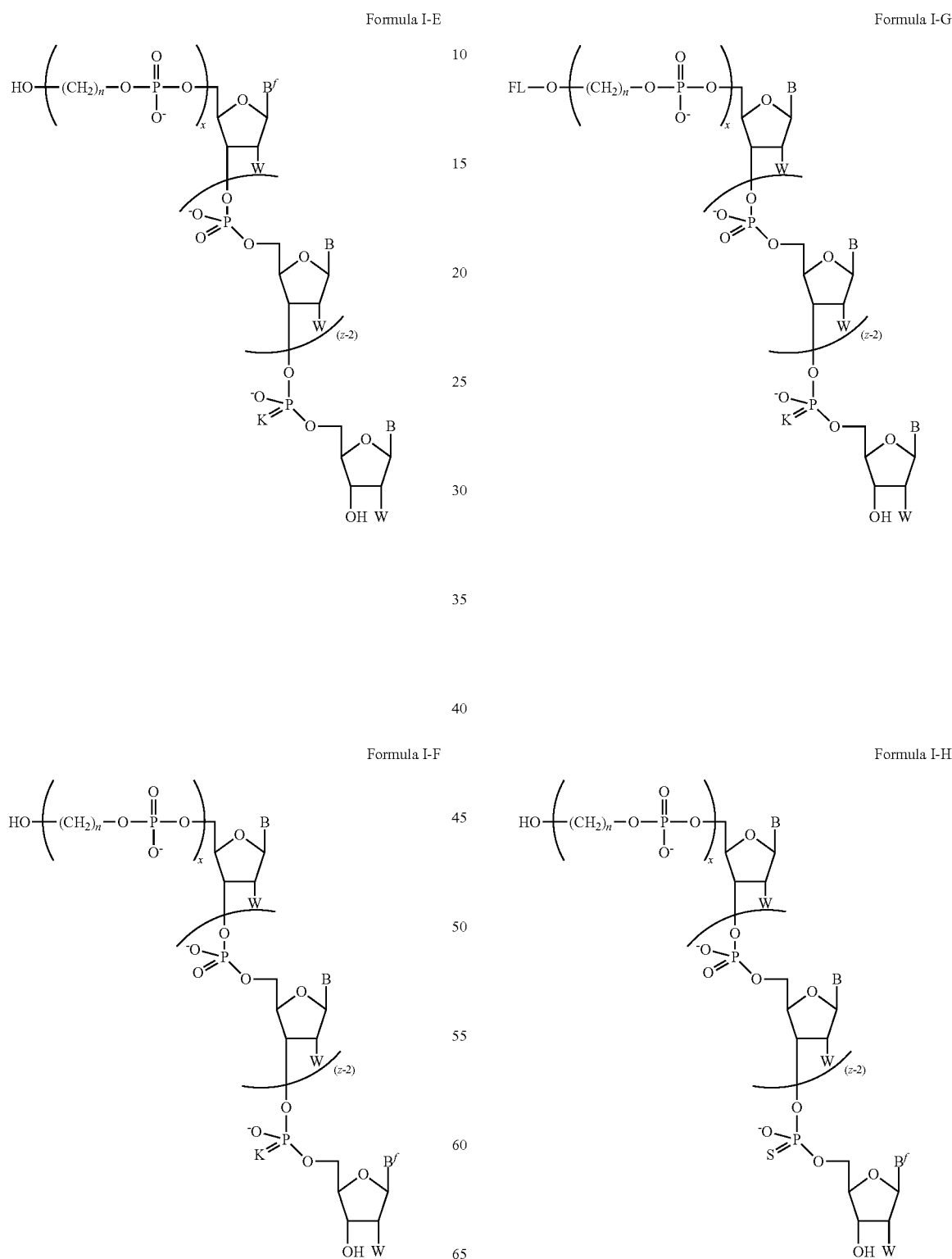

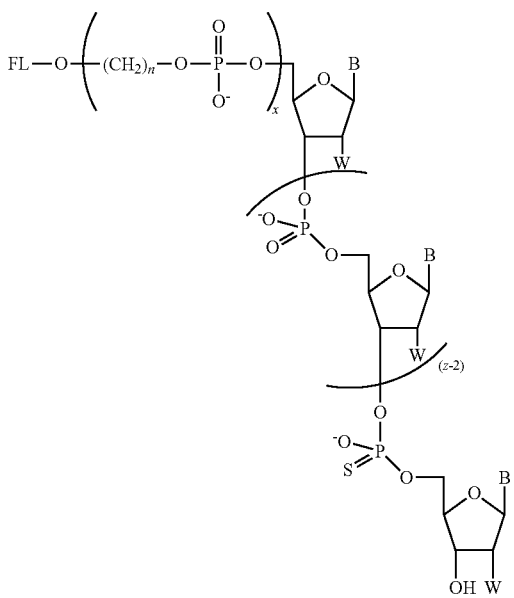

Formula I-J

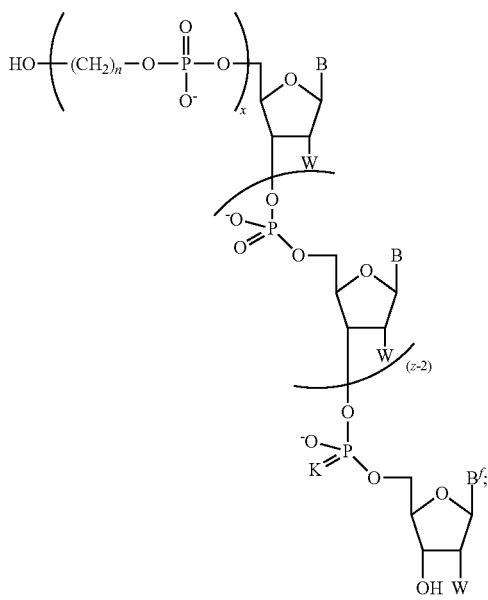

Formula I-K wherein FL is a dye label and B is a dye labeled nucleobase. Fl and B$^f$ may each represent a fluorescent dye label.

For the chemically-enhanced primer of Formula I, each n can independently be an integer of 1 to 12. In some embodiments, n is 1, 2, 3, 4, 5, 6, 7, 8, or 9. In some embodiments, n is 3. In other embodiments, n is 4. Alternatively, n may be 6. In some embodiments of the chemically enhanced primer of Formula I, when x is greater than 2, a first instance of n is selected to be 3 and a second instance of n is selected to be 6. In further embodiments of the chemically-enhanced primers of Formula I, when x is greater than 2, more than one instance of n is selected to be 3, and more than one instance of n is selected to be 6. In yet other embodiments, when x is greater than 5, a plurality of n is selected to be 3, and a second plurality of n is selected to be 6.

The chemically-enhanced primer of Formula I may have m=1 or m=0. In some embodiments the chemically-enhanced primer of Formula I has m=0.

The chemically-enhanced primer of Formula I may have x, wherein x is an integer of 1 to about 50. In some of the embodiments of the chemically-enhanced primer of Formula I, x is 1, 2, 3, 4, 5, 6, 7, 8, 9, or 10. In other embodiments, x is 10, 15, 18, 20 or 24. In some embodiments, x is 5, 8, 9, 10 or 15. In other embodiments, x is 11, 12, 13, 14, 17 or 20. In other embodiments, x is 30. In further embodiments, x is at least 5, at least 6, at least 8, at least 9, at least 10, at least 15 at least 18, at least 20, or at least 24. In some embodiments, x is 15. In yet other embodiments, x is 8 or 9.

In some embodiments, the chemically-enhanced primers comprise a second plurality y of

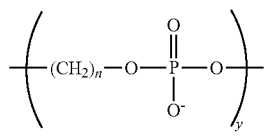

moieties, wherein y is an integer of 1-20. In some embodiments, when a first plurality x of n has a value of a first integer, then a second plurality y of n is an integer of 1 to 20. In some embodiments, the chemically-enhanced primer may have a first plurality of n wherein n is 3 and x is 15, and a second plurality of n wherein n is 6 and x is 5. All combinations of n, x and y are contemplated for use in the chemically-enhanced primers of Formula I.

In the chemically-enhanced primer of Formula I, z is an integer of 3 to about 100. In some embodiments, z is an integer of 5 to 50, 5 to 40, or 5 to about 30. In other embodiments, z is an integer of 5 to 25, or 5 to 20.

In some of the embodiments of the chemically-enhanced primer of Formula I, K is S. In other embodiments, K is O.

In some embodiments of the chemically-enhanced primer of Formula I, W is H or OH.

The chemically-enhanced primer of Formula I, I-B, I-C, I-E, I-F, or I-G, may have any combination of B, B$^f$, FL, K, m, n, W, x, and z of the ranges and selections disclosed above.

The chemically-enhanced primer of Formula I-D may have any combination of B, FL, K, m, n, W, x, and z of the ranges and selections disclosed above The chemically-enhanced primer of Formula I-A, I-H, I-J or I-K, may have any combination of B, B$^f$, FL, K, m, n, W, x, and z of the ranges and selections disclosed above.

In other embodiments, the chemically-enhanced primer is a compound having a structure of Formula II:

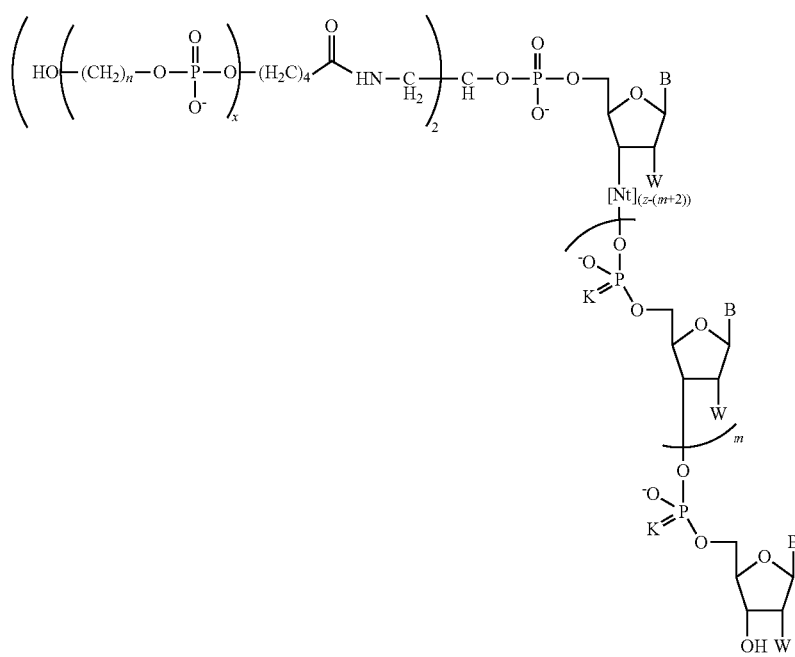

Formula II wherein B is a nucleobase; K is S or O; each n is independently an integer of 1 to 12; m is 0 or 1; x is an integer of 1 to about 50; z is an integer of 3 to about 100; W is OH, F, OMe, or H; and Nt is a moiety having a formula:

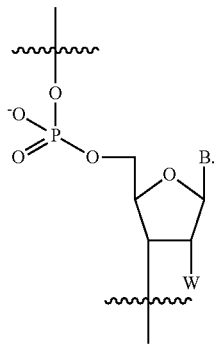

The chemically-enhanced primer of Formula II may be referred to as a doubler, and represents a branched arrangement of NCM moieties.

The chemically-enhanced primer of Formula II may comprise one or more B, wherein B is a naturally occurring nucleobase. In other embodiments, the chemically-enhanced primer of Formula II may comprise one or more B, wherein B is a nucleobase analog.

The chemically-enhanced primer of Formula II may have only one phosphothiorate linkage, wherein m is 0.

The chemically-enhanced primer of Formula II may be labeled with a dye, including dyes that are fluorescent. The chemically-enhanced primer of Formula II may include one or more B labeled with a dye, and is represented as $B^f$. In some embodiments, the 3' terminal nucleotide of the chemically-enhanced primer has a fluorescently labeled B. The chemically-enhanced primer may contain a 3' fluorescently labeled terminal nucleotide wherein the B of the 3' terminal nucleotide is a nucleobase analog. Alternatively, the chemically-enhanced primer may contain a 5' terminal nucleotide having a fluorescently labeled B, which can be represented as B. In some embodiments, wherein the chemically-enhanced primer contains a 5' terminal nucleotide containing the fluorescently labeled nucleobase, $B^f$, the labeled nucleobase is a nucleobase analog. In other embodiments, the chemically-enhanced primer may contain a fluorescently labeled NCM attached directly or indirectly to one of a plurality of NCMs and/or a linker moiety to the 5' terminal nucleotide of the primer. Additionally, the chemically-enhanced primer of Formula II may be fluorescently labeled on the nucleobase of a nucleotide located at an internal position of the oligonucleotide, and the internal fluorescently labeled nucleotide may be selected to be at any position of the non-terminal portion of the oligonucleotide.

For the chemically-enhanced primer of Formula II, n can be an integer of 1 to 9. In some embodiments, n is 1, 2, 3, 4, 5, 6, 7, 8, or 9. In some embodiments, n is 3. In other embodiments, n is 4. Alternatively, n may be 6. In some embodiments of the chemically-enhanced primer of Formula II, when x is greater than 2, a first instance of n is selected to be 3 and a second instance of n is selected to be 6. In further embodiments of the chemically-enhanced primers of Formula I, when x is greater than 2, more than one instance of n is selected to be 3, and more than one instance of n is selected to be 6. In yet other embodiments, when x is greater than 5, a plurality of n is selected to be 3, and a second plurality of n is selected to be 6.

The chemically-enhanced primer of Formula II may have m=1 or m=0. In some embodiments the chemically-enhanced primer of Formula II has m=0.

The chemically-enhanced primer of Formula II may have x wherein x is an integer of 1 to about 50. In some of the embodiments of the chemically-enhanced primer of Formula II, x is 1, 2, 3, 4, 5, 6, 7, 8, 9, or 10. In other embodiments, x is 10, 15, 18, 20 or 24. In some embodiments, x is 5, 8, 9, 10 or 15. In other embodiments, x is 11, 12, 13, 14, 17 or 20. In other embodiments, x is 30. In further embodiments, x is at least 5, at least 6, at least 8, at least 9, at least 10, at least 15 at least 18, at least 20, or at least 24. In some embodiments, x is 15. In yet other embodiments, x is 8 or 9.

In some embodiments, the chemically-enhanced primers comprise a second plurality y of

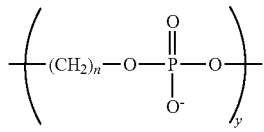

moieties, wherein y is an integer of 1-20. In some embodiments, when a first plurality x of n has a value of a first integer, then a second plurality y of n is an integer of 1 to 20. In some embodiments, the chemically-enhanced primer may have a first plurality of n wherein n is 3 and x is 15, and a second plurality of n wherein n is 6 and x is 5. All combinations of n, x and y are contemplated for use in the chemically-enhanced primers of Formula II.

In the chemically-enhanced primer of Formula II, z is an integer of 3 to about 100. In some embodiments, z is an integer of 5 to 50, 5 to 40, or 5 to about 30. In other embodiments, z is an integer of 5 to 25, or 5 to 20.

In some of the embodiments of the chemically-enhanced primer of Formula II, K is S. In other embodiments, K is O.

In some embodiments of the chemically-enhanced primer of Formula II, W is H or OH.

The chemically-enhanced primer of Formula II may have any combination of B, K, m, n, W, x, and z of the ranges and selections disclosed above.

In yet other embodiments, the chemically-enhanced primer is a compound having a structure of the Formula III:

wherein B is a nucleobase; K is S or O; each n is independently an integer of 1 to 12; m is 0 or 1; x is an integer of 1 to about 50; z is an integer of 3 to about 100; W is OH, F, OMe, or H; and Nt is a moiety having a formula:

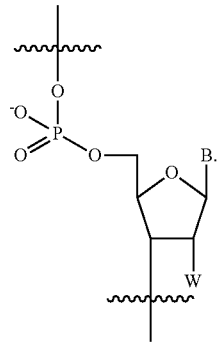

The chemically-enhanced primer of Formula III may be referred to as a trebler and represents a branched arrangement of NCM moieties.

The chemically-enhanced primer of Formula III may comprise one or more B, wherein B is a naturally occurring nucleobase. In other embodiments, the chemically-enhanced primer of Formula III may comprise one or more B, wherein B is a nucleobase analog.

The chemically-enhanced primer of Formula III may have only one phosphothiorate linkage, wherein m is 0.

The chemically-enhanced primer of Formula III may be labeled with a dye, including dyes that are fluorescent. The chemically-enhanced primer of Formula III may include one or more B labeled with a dye, and is represented as $B^f$. In some embodiments, the 3' terminal nucleotide of the chemically-enhanced primer has a fluorescently labeled B. The chemically-enhanced primer may contain a 3' fluorescently labeled terminal nucleotide wherein the B of the 3' terminal nucleotide is a nucleobase analog. Alternatively, the chemically-enhanced primer may contain a 5' terminal nucleotide having a fluorescently labeled B, which can be represented as $B^f$. In some embodiments, wherein the chemically-enhanced primer contains a 5' terminal nucleotide containing the fluorescently labeled nucleobase, $B^f$, the labeled nucleobase is a nucleobase analog. In other embodiments, the chemically-enhanced primer may contain a fluorescently labeled NCM attached directly or indirectly to one of a plurality of NCMs and/or a linker moiety to the 5' terminal nucleotide of the primer. Additionally, the chemically-enhanced primer of Formula II may be fluorescently labeled on the nucleobase of a nucleotide located at an internal position of the oligonucleotide, and the internal fluorescently labeled nucleotide may be selected to be at any position of the non-terminal portion of the oligonucleotide.

For the chemically-enhanced primer of Formula III, n can be an integer of 1 to 9. In some embodiments, n is 1, 2, 3, 4, 5, 6, 7, 8, or 9. In some embodiments, n is 3. In other embodiments, n is 4. Alternatively, n may be 6. In some embodiments of the chemically-enhanced primer of Formula III, when x is greater than 2, a first instance of n is selected to be 3 and a second instance of n is selected to be 6. In further embodiments of the chemically-enhanced primers of Formula III, when x is greater than 2, more than one instance of n is selected to be 3, and more than one instance of n is selected to be 6. In yet other embodiments, when x is greater than 5, a plurality of n is selected to be 3, and a second plurality of n is selected to be 6.

The chemically-enhanced primer of Formula III may have m=1 or m=0. In some embodiments the chemically-enhanced primer of Formula III has m=0.

The chemically-enhanced primer of Formula III may have x wherein x is an integer of 1 to about 30. In some of the embodiments of the chemically-enhanced primer of Formula II, x is 1, 2, 3, 4, 5, 6, 7, 8, 9, or 10. In other embodiments, x is 10, 15, 18, 20 or 24. In some embodiments, x is 5, 8, 9, 10 or 15. In other embodiments, x is 11, 12, 13, 14, 17 or 20. In other embodiments, x is 30. In further embodiments, x is at least 5, at least 6, at least 8, at least 9, at least 10, at least 15 at least 18, at least 20, or at least 24. In some embodiments, x is 15. In yet other embodiments, x is 8 or 9.

In the chemically-enhanced primer of Formula III, z is an integer of 3 to about 100. In some embodiments, z is an integer of 5 to 50, 5 to 40, or 5 to about 30. In other embodiments, z is an integer of 5 to 25, or 5 to 20.

In some embodiments, the chemically-enhanced primers comprise a second plurality y of

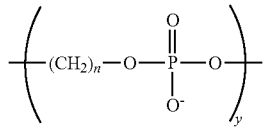

moieties, wherein y is an integer of 1-20. In some embodiments, when a first plurality x of n has a value of a first integer, then a second plurality y of n is an integer of 1 to 20. In some embodiments, the chemically-enhanced primer may have a first plurality of n wherein n is 3 and x is 15, and a second plurality of n wherein n is 6 and x is 5. All combinations of n, x and y are contemplated for use in the chemically-enhanced primers of Formula III.

In some of the embodiments of the chemically-enhanced primer of Formula III, K is S. In other embodiments, K is O.

In some embodiments of the chemically-enhanced primer of Formula III, W is H or OH.

The chemically-enhanced primer of Formula III may have any combination of B, K, m, n, W, x, and z of the ranges and selections disclosed above.

Other embodiments of the chemically-enhanced primer are represented by Formula IV:

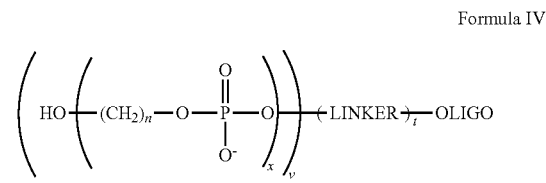

Formula IV wherein each instance of n is independently an integer of 1 to 12; x is an integer of 1 to 50; v is an integer of 1 to 9; t is 0 or 1; LINKER comprises 3-100 atoms;
OLIGO has a structure of the following formula:

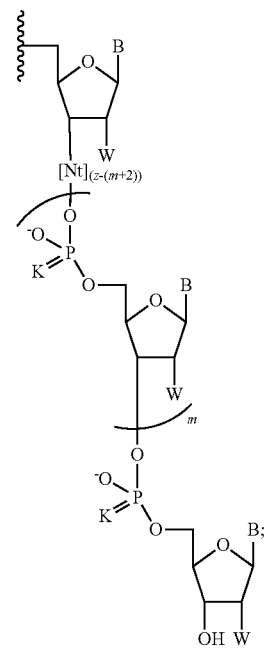

wherein B is a nucleobase; K is S or O; m is 0 or 1; z is an integer of 3 to about 100; W is OH, F, OMe, or H; and Nt is a moiety having a formula:

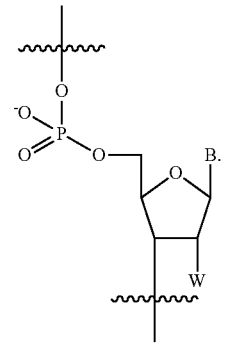

The chemically-enhanced primer of Formula IV, may comprise one or more B wherein B is a naturally occurring nucleobase. In other embodiments, the chemically-enhanced primer of Formula IV may comprise one or more B, wherein B is a nucleobase analog.

The chemically-enhanced primer of Formula IV may be labeled with a dye, including dyes that are fluorescent. The chemically-enhanced primer having a formula of $(Cn)_x$-OLIGO may include one or more B labeled with a dye, and is represented as $B^f$. In some embodiments, when the chemically-enhanced primer has at least one B labeled with a dye, the B may be a nucleobase analog. In some embodiments, the 3' terminal nucleotide of the chemically-enhanced primer has a fluorescently labeled B, which can be represented as $B^f$. Alternatively, the chemically-enhanced primer may contain a 5' terminal nucleotide having a fluorescently labeled B, which can be represented as $B^f$. Additionally, the chemically-enhanced primer having a formula of $(Cn)_x$-OLIGO, may be fluorescently labeled on the nucleobase of a nucleotide located at an internal position of the oligonucleotide, and the internal fluorescently labeled nucleotide may be selected to be at any position of the non-terminal portion of the oligonucleotide. In other embodiments, the chemically-enhanced primer may contain a fluorescently labeled NCM attached directly or indirectly to one of a plurality of NCMs and/or to a NCM linker moiety forming a covalent attachment to the 5' terminal nucleotide of the primer.

LINKER is an NCM linker and may comprise 3-100 atoms and include ether, amide, phosphodiester, and ester moieties to form a covalent linkage between the NCM and the oligonucleotide. LINKER may be attached to the 5' carbon of the ribose of the nucleotide at the 5' terminus of the oligonucleotide. In some embodiments, LINKER is present. In other embodiments the NCM phosphodiester moiety or moieties are directly attached to OLIGO.

For the chemically-enhanced primer of Formula IV, v can be an integer of 1 to 9. In some embodiments, v is 1. In other embodiments, v is 2. In yet other embodiments, v is 3.

For the chemically-enhanced primer of Formula IV, n can be an integer of 1 to 12. In some embodiments, n is 1, 2, 3, 4, 5, 6, 7, 8, or 9. In other embodiments, n is an integer of 1 to 9. In some embodiments, n is 3. In other embodiments, n is 4. Alternatively, n may be 6 The chemically-enhanced primer of Formula IV has x, wherein x is an integer of 1 to about 30. In some of the embodiments of the chemically-enhanced primer of Formula IV, x is 1, 2, 3, 4, 5, 6, 7, 8, 9, or 10. In other embodiments, x is 10, 15, 18, 20 or 24. In some embodiments, x is 5, 8, 9, 10 or 15. In other embodiments, x is 11, 12, 13, 14, 17 or 20. In further embodiments, x is at least 5, at least 6, at least 8, at least 9, at least 10, at least 15 at least 18, at least 20, or at least 24. In some embodiments, x is 15. In yet other embodiments, x is 8 or 9.

In some embodiments of the chemically-enhanced primer of Formula IV, when x is greater than 2, a first instance of n is selected to be 3 and a second instance of n is selected to be 6. In further embodiments of the chemically-enhanced primers of Formula IV, when x is greater than 2, more than one instance of n is selected to be 3, and more than one instance of n is selected to be 6. In yet other embodiments, when x is greater than 5, a plurality of n is selected to be 3, and a second plurality of n is selected to be 6.

In some embodiments, the chemically-enhanced primers comprise a second plurality y of

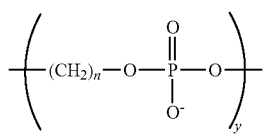

moieties, wherein y is an integer of 1-20. In some embodiments, when a first plurality x of n has a value of a first integer, then a second plurality y of n is an integer of 1 to 20. In some embodiments, the chemically-enhanced primer may have a first plurality of n wherein n is 3 and x is 15, and a second plurality of n wherein n is 6 and x is 5. All combinations of n, x and y are contemplated for use in the chemically-enhanced primers of Formula IV.

The chemically-enhanced primer having a formula of Formula IV has m=1 or m=0. In some embodiments the chemically-enhanced primer of Formula IV has m=0.

The chemically-enhanced primer having a formula of Formula IV has z, wherein z is an integer of 3 to about 100. In some embodiments, z is an integer of 5 to 50, 5 to about 40, or 5 to about 30. In other embodiments, z is an integer of 5 to 25, or 5 to 20.

In some of the embodiments of the chemically-enhanced primer of Formula IV, K is S. In other embodiments, K is O.

In some embodiments of the chemically-enhanced primer of Formula IV, W is H or OH.

The chemically-enhanced primer of Formula IV, may have any combination of B, n, t, v, x, m, y, z, K or W of the ranges and selections disclosed above.

In some embodiments, the chemically-enhanced primer of Formula IV is a chemically-enhanced primer $(Cn)_x$-OLIGO, wherein $(Cn)_x$ has a structure of the following formula:

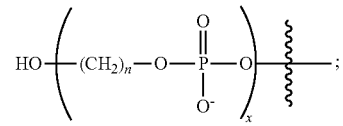

wherein each instance of n is independently an integer of 1 to 12; and x is an integer of 1 to about 30; and OLIGO has a structure of the following formula:

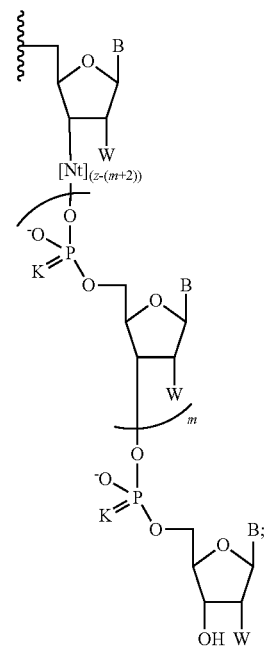

wherein B, K, m, z, y, Nt, and W are as defined above for Formula IV.

For the chemically-enhanced primer having a formula of $(Cn)_x$-OLIGO, v is 1, t is 0, no LINKER is present, and the chain of NCM moieties are attached to OLIGO directly.

The chemically-enhanced primer having a formula of $(Cn)_x$-OLIGO, may have any combination of B, n, x, m, z, K or W of the ranges and selections disclosed above for Formula IV.

In yet other embodiments, the chemically-enhanced primer is represented by the following formulae: $(Cn)_x$-OLIGO, wherein $(Cn)_x$ has a structure of the following formula:

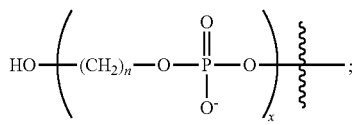

wherein each instance of n is independently an integer of 1 to 12; and x is an integer of 1 to about 30; OLIGO* has a structure of the following formula:

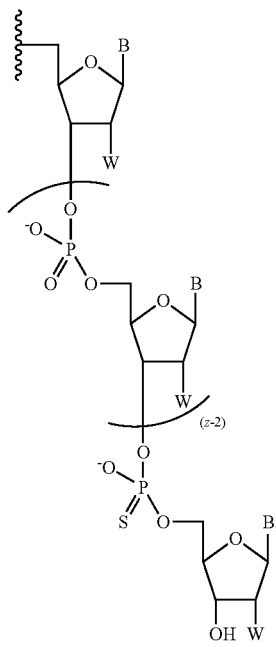

wherein B, K, m, z, y, Nt, and W are as defined above for Formula IV.

For the chemically-enhanced primer having a formula of $(Cn)_x$-OLIGO*, v is 1, t is 0, no LINKER is present, and the chain of NCM moieties are attached to OLIGO* directly.

The chemically-enhanced primer having a formula of $(Cn)_x$-OLIGO*, may have any combination of B, n, x, m, z, or W of the ranges and selections disclosed above for Formula IV.

Chemically-enhanced primers having a formula of $(Cn)_x$ Formula VI-A1 include, but are not limited to:

$(Cn)_x$-US1, where n is 1 to 9 and x is 1 to about 30.

In some embodiments, $(Cn)_x$-US1 is $(C3)_1$-US1, $(C3)_2$-US1, $(C3)_3$-US1, $(C3)_4$-US1, $(C3)_5$-US1, $(C3)_6$-US1, $(C3)_7$-US1, $(C3)_8$-US1, $(C3)_9$-US1, $(C3)_{10}$-US1, $(C3)_{11}$-US1, $(C3)_{12}$-US1, $(C3)_{13}$-US1, $(C3)_{14}$-US1, $(C3)_{15}$-US1, $(C3)_{16}$-US1, $(C3)_{17}$—US1, $(C3)_{18}$-US1, $(C3)_{21}$-US1, $(C3)_{24}$-US1, $(C3)_{27}$-US1, or $(C3)_{30}$-US1. In some embodiments, $(Cn)_x$-US1 is a forward primer and may have any x as described above. In other embodiments, $(Cn)_x$-US1 is a reverse primer and may have any x as described above.

$(Cn)_x$-M13-Forward, where n is 1 to 9 and x is 1 to about 30.

In some embodiments, $(Cn)_x$-M13-forward is $(C3)_1$-M13-forward, $(C3)_2$-M13-forward, $(C3)_3$-M13-forward, $(C3)_4$-M13-forward, $(C3)_5$-M13-forward, $(C3)_6$-M13-forward, $(C3)_7$-M13-forward, $(C3)_8$-M13-forward, $(C3)_9$-M13-forward, $(C3)_{10}$-M13-forward, $(C3)_{11}$-M13-forward, $(C3)_{12}$-M13-forward, $(C3)_{13}$-M13-forward, $(C3)_{14}$-M13-forward, $(C3)_{15}$-M13-forward, $(C3)_{16}$-M13-forward, $(C3)_{17}$-M13-forward, $(C3)_{18}$-M13-forward, $(C3)_{21}$-M13-forward, $(C3)_{24}$-M13-forward, $(C3)_{27}$-M13-forward, or $(C3)_{30}$-M13-forward.

$(Cn)_x$-M13-Reverse, where n is 1 to 9 and x is 1 to about 30.

In some embodiments, $(Cn)_x$-M13-reverse is $(C3)_1$-M13-reverse, $(C3)_2$-M13-reverse, $(C3)_3$-M13-reverse, $(C3)_4$-M13-reverse, $(C3)_5$-M13-reverse, $(C3)_6$-M13-reverse, $(C3)_7$-M13-reverse, $(C3)_8$-M13-reverse, $(C3)_9$-M13-reverse, $(C3)_{10}$-M13-reverse, $(C3)_{11}$-M13-reverse, $(C3)_{12}$-M13-reverse, $(C3)_{13}$-M13-reverse, $(C3)_{14}$-M13-reverse, $(C3)_{15}$-M13-reverse, $(C3)_{16}$-M13-reverse, $(C3)_{17}$-M13-reverse, $(C3)_{18}$-M13-reverse, $(C3)_{21}$-M13-reverse, $(C3)_{24}$-M13-reverse, $(C3)_{27}$-M13-reverse, or $(C3)_{30}$-M13-reverse.

$(Cn)_x$-T7, where n is 1 to 9 and x is 1 to about 30.

In some embodiments, $(Cn)_x$-T7 is $(C3)_1$-T7, $(C3)_2$-T7, $(C3)_3$-T7 $(C3)_4$-T7, $(C3)_5$-T7, $(C3)_6$-T7, $(C3)_7$-T7, $(C3)_8$-T7, $(C3)_9$-T7, $(C3)_{10}$-T7, $(C3)_{11}$-T7, $(C3)_{12}$-T7, $(C3)_{13}$-T7, $(C3)_{14}$-T7, $(C3)_{15}$-T7, $(C3)_{16}$-T7, $(C3)_{17}$-T7, $(C3)_{18}$-T7, $(C3)_{21}$-T7, $(C3)_{24}$-T7, $(C3)_{27}$-T7, or $(C3)_{30}$-T7. In some embodiments, $(Cn)_x$-T7 is a forward primer and may have any x as described above. In other embodiments, $(Cn)_x$-T7 is a reverse primer and may have any x as described above.

$(Cn)_x$-SP6, where n is 1 to 9 and x is 1 to about 30.

In some embodiments, $(Cn)_x$-SP6 is $(C3)_1$-SP6, $(C3)_2$-SP6, $(C3)_3$-SP6, $(C3)_4$-SP6, $(C3)_5$-SP6, $(C3)_6$-SP6, $(C3)_7$-SP6, $(C3)_8$-SP6, $(C3)_9$-SP6, $(C3)_{10}$-SP6, $(C3)_{11}$-SP6, $(C3)_{12}$-SP6, $(C3)_{13}$-SP6, $(C3)_{14}$-SP6, $(C3)_{15}$-SP6, $(C3)_{16}$-SP6, $(C3)_{17}$-SP6, $(C3)_{18}$-SP6, $(C3)_{21}$-SP6, $(C3)_{24}$-SP6, $(C3)_{27}$-SP6, or $(C3)_{30}$-SP6. In some embodiments, $(Cn)_x$-SP6 is a forward primer and may have any x as described above. In other embodiments, $(Cn)_x$-SP6 is a reverse primer and may have any x as described above.

$(Cn)_x$-T3, where n is 1 to 9 and x is 1 to about 30.

In some embodiments, $(Cn)_x$ T3 is $(C3)_1$-T3, $(C3)_2$-T3, $(C3)_3$-T3, $(C3)_4$-T3, $(C3)_5$-T3, $(C3)_6$-T3, $(C3)_7$-T3, $(C3)_8$-T3, $(C30)_9$-T3, $(C3)_{10}$-T3, $(C3)_{11}$-T3, $(C3)_{12}$-T3, $(C3)_{13}$-T3, $(C3)_{14}$-T3, $(C3)_{15}$-T3, $(C3)_{16}$-T3, $(C3)_{17}$-T3, $(C3)_{18}$-T3, $(C3)_{21}$-T3, $(C3)_{24}$-T3, $(C3)_{27}$-T3, or $(C3)_{30}$-T3. In some embodiments, $(Cn)_x$-T3 is a forward primer and may have any x as described above. In other embodiments, $(Cn)_x$-T3 is a reverse primer and may have any x as described above.

$(Cn)_x$-GSO, where n is 1 to 9, x is 1 to about 30, and GSO is a Gene Specific Oligonucleotide Sequence, Wherein the Gene Specific Oligonucleotide Comprises 50 or Fewer Nucleotides.

In some embodiments, $(Cn)_x$ GSO is $(C3)_1$-GSO, $(C3)_2$-GSO, $(C3)_3$-GSO, $(C3)_4$-GSO, $(C3)_5$-GSO, $(C3)_6$-GSO, $(C3)_7$-GSO, $(C3)_8$-GSO, $(C3)_9$-GSO, $(C3)_{10}$-GSO, $(C3)_{11}$-GSO, $(C3)_{12}$-GSO, $(C3)_{13}$-GSO, $(C3)_{14}$-GSO, $(C3)_{15}$-GSO, $(C3)_{16}$-GSO, $(C3)_{17}$-GSO, $(C3)_{18}$-GSO, $(C3)_{21}$-GSO, $(C3)_{24}$-GSO, $(C3)_{27}$-GSO, or $(C3)_{30}$-GSO. In some embodiments, $(Cn)_x$-GSO is a forward primer and may have any x as described above. In other embodiments, $(Cn)_x$-GSO is a reverse primer and may have any x as described above.

Chemically-enhanced primers having a formula of $(Cn)_x$-OLIGO* include, but are not limited to:

$(Cn)_x$-US1*, where n is 1 to 9 and x is 1 to about 30.

In some embodiments, $(Cn)_x$-US1* is $(C3)_1$-US1*, $(C3)_2$-US1*, $(C3)_3$-US1*, $(C3)_4$-US1*, $(C3)_5$-US1*, $(C3)_6$-US1', $(C3)_7$-US1*, $(C3)_8$-US1*, $(C3)_9$-US1*, $(C3)_{10}$-US1*, $(C3)_{11}$-US1*, $(C3)_{12}$-US1*, $(C3)_{13}$-US1*, $(C3)_{14}$-US1v, $(C3)_{15}$-US1*, $(C3)_{16}$-US1*, $(C3)_{17}$-US1*, $(C3)_{18}$-US1*, $(C3)_{21}$-US1*, $(C3)_{24}$-US1*, $(C3)_{27}$-US1*, or $(C3)_{30}$-US1*. In some embodiments, $(Cn)_x$-US1* is a forward primer and may have any x as described above. In other embodiments, $(Cn)_x$-US1* is a reverse primer and may have any x as described above.

$(Cn)_x$-M13*-Forward, where n is 1 to 9 and x is 1 to about 30.

In some embodiments, $(Cn)_x$-M13*-forward is $(C3)_1$-M13*-forward, $(C3)_2$-M13*-forward, $(C3)_3$-M13*-forward, $(C3)_4$-M13*-forward, $(C3)_5$-M13*-forward, $(C3)_6$-M13*-forward, $(C3)_7$-M13*-forward, $(C3)_8$-M13*-forward, $(C3)_9$-M13*-forward, $(C3)_{10}$-M13*-forward, $(C3)_{11}$-M13*-forward, $(C3)_{12}$-M13*-forward, $(C3)_{13}$-M13*-forward, $(C3)_{14}$-M13*-forward, $(C3)_{15}$-M13*-forward, $(C3)_{16}$-M13*-forward, $(C3)_{17}$-M13*-forward, $(C3)_{18}$-M13*-forward, $(C3)_{21}$-M13*-forward, $(C3)_{24}$-M13*-forward, $(C3)_{27}$-M13*-forward, or $(C3)_{30}$-M13*-forward.

$(Cn)_x$-M13*-Reverse, where n is 1 to 9 and x is 1 to about 30.

In some embodiments, $(Cn)_x$-M13*-reverse is $(C3)_1$-M13*-reverse, $(C3)_2$-M13*-reverse, $(C3)_3$-M13*-reverse, $(C3)_4$-M13*-reverse, $(C3)_5$-M13*-reverse, $(C3)_6$-M13*-reverse, $(C3)_7$-M13*-reverse, $(C3)_8$-M13*-reverse, $(C3)_9$-M13*-reverse, $(C3)_{10}$-M13*-reverse, $(C3)_{11}$-M13*-reverse, $(C3)_{12}$-M13*-reverse, $(C3)_{13}$-M13*-reverse, $(C3)_{14}$-M13*-reverse, $(C3)_{15}$-M13*-reverse, $(C3)_{16}$-M13*-reverse, $(C3)_{17}$-M13*-reverse, $(C3)_{18}$-M13*-reverse, $(C3)_{21}$-M13*-reverse, $(C3)_{23}$-M13*-reverse, $(C3)_{27}$-M13*-reverse, or $(C3)_{30}$-M13*-reverse.

$(Cn)_x$-T7*, where n is 1 to 9 and x is 1 to about 30.

In some embodiments, $(Cn)_x$-T7* is $(C3)_1$-T7*, $(C3)_2$-T7 $(C3)_3$-T7*, $(C3)_4$-T7*, $(C3)_5$-T7*, $(C3)_6$-T7*, $(C3)_7$-T7*, $(C3)_8$-T7*, $(C3)_9$-T7*, $(C3)_{10}$-T7*, $(C3)_{11}$-T7*, $(C3)_{12}$-T7*, $(C3)_{13}$-T7*, $(C3)_{14}$-T7*, $(C3)_{15}$-T7*, $(C3)_{16}$-T7*, $(C3)_{17}$-T7*, $(C3)_{18}$-T7*, $(C3)_{21}$-T7*, $(C3)_{24}$-T7*, $(C3)_{27}$-T7*, or $(C3)_{30}$-T7*. In some embodiments, $(Cn)_x$-T7* is a forward primer and may have any x as described above. In other embodiments, $(Cn)_x$-T7* is a reverse primer and may have any x as described above.

$(Cn)_x$-SP6*, where n is 1 to 9 and x is 1 to about 30.

In some embodiments, $(Cn)_x$-SP6* is $(C3)_1$-SP6*, $(C3)_2$-SP6*, $(C3)_3$-SP6*, $(C3)_4$-SP6*, $(C3)_5$-SP6*, $(C3)_6$-SP6*, $(C3)_7$-SP6*, $(C3)_8$-SP6*, $(C3)_9$-SP6*, $(C3)_{10}$-SP6*, $(C3)_{11}$-SP6*, $(C3)_{12}$-SP6*, $(C3)_{13}$-SP6*, $(C3)_{14}$-SP6*, $(C3)_{15}$-SP6*, $(C3)_{16}$-SP6*, $(C3)_{17}$-SP6*, $(C3)_{18}$-SP6*, $(C3)_{21}$-SP6*, $(C3)_{24}$-SP6*, $(C3)_{27}$-SP6*, or $(C3)_{30}$-SP6*. In some embodiments, $(Cn)_x$-SP6* is a forward primer and may have any x as described above. In other embodiments, $(Cn)_x$-SP6* is a reverse primer and may have any x as described above.

$(Cn)_x$-T3*, where n is 1 to 9 and x is 1 to about 30.

In some embodiments, $(Cn)_x$ T3* is $(C3)_1$-T3*, $(C3)_2$-T3*, $(C(C3)_3$-T3*, $(C3)_4$-T3*, $(C3)_5$-T3*, $(C3)_6$-T3*, $(C3)_7$-T3*, $(C3)_8$-T3*, $(C3)_9$-T3*, $(C3)_{10}$-T3*, $(C3)_{11}$-T3*, $(C3)_{12}$-T3*, $(C3)_{13}$-T3*, $(C3)_{14}$-T3*, $(C3)_{15}$-T3*, $(C3)_{16}$-T3*, $(C3)_{17}$-T3*, $(C3)_{18}$-T3*, $(C3)_{21}$-T3*, $(C3)_{24}$-T3*, $(C3)_{27}$-T3*, or $(C3)_{30}$-T3*. In some embodiments, $(Cn)_x$-T3* is a forward primer and may have any x as described above. In other embodiments, $(Cn)_x$-T3* is a reverse primer and may have any x as described above.

$(Cn)_x$-GSO*, where n is 1 to 9, x is 1 to about 30, and GSO* is a Gene Specific Oligonucleotide Sequence, Wherein the Gene Specific Oligonucleotide Comprises 50 or Fewer Nucleotides.

In some embodiments, $(Cn)_x$ GSO* is $(C3)_1$-GSO*, $(C3)_2$-GSO*, $(C3)_3$-GSO*, $(C3)_4$-GSO*, $(C3)_5$-GSO*, $(C3)_6$-GSO*, $(C3)_7$-GSO*, $(C3)_8$-GSO*, $(C3)_9$-GSO*, $(C3)_{10}$-GSO*, $(C3)_{11}$-GSO*, $(C3)_{12}$-GSO*, $(C3)_{13}$-GSO*, $(C3)_{14}$-GSO*, $(C3)_{15}$-GSO*, $(C3)_{16}$-GSO*, $(C3)_{17}$-GSO*, $(C3)_{18}$-GSO*, $(C3)_{21}$-GSO*, $(C3)_{24}$-GSO*, $(C3)_{27}$-GSO*, or $(C3)_{30}$-GSO*. In some embodiments, $(Cn)_x$-GSO* is a forward primer and may have any x as described above. In other embodiments, $(Cn)_x$-GSO* is a reverse primer and may have any x as described above.

In further embodiments, the chemically-enhanced primer of Formula IV may be a doubler, and has a structure of Formula V:

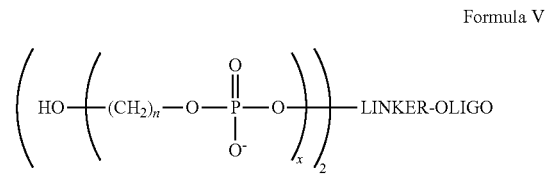

Formula V wherein t is 1; LINKER is present; v is 2; and OLIGO, x, and n are as defined above for Formula IV.

One example of a chemically-enhanced primer of Formula V has a structure of Formula V-A:

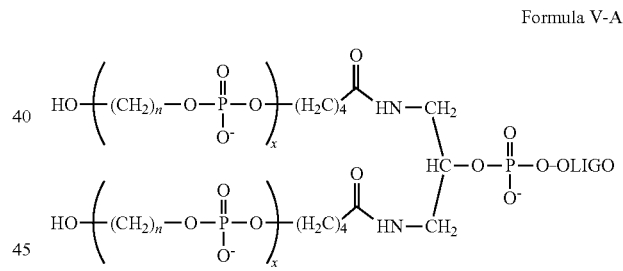

Formula V-A wherein n, x, and OLIGO are as defined above for Formula IV, and LINKER has a structure of the following formula:

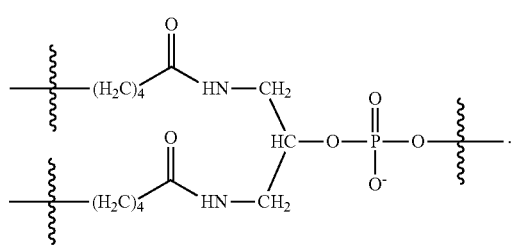

The chemically-enhanced primer of Formula V-A may have any combination of B, n, x, m, y, z, K or W of the ranges and selections disclosed above for Formula IV.

In yet another embodiment, the chemically-enhanced primer of Formula IV may be a trebler and have a structure of Formula VI:

Formula VI

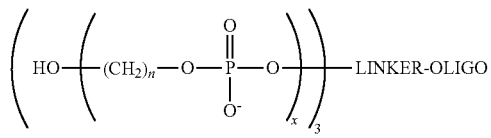

wherein t is 1; LINKER is present; v is 3; and OLIGO, x, and n are as defined above for Formula IV. One group of chemically-enhanced primers of Formula VI have structures of Formula VI-A:

Formula VI-A

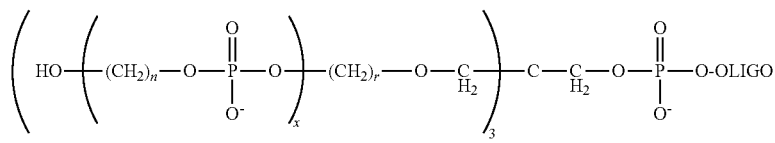

wherein r is an integer of 2 to 9; and n, x, and OLIGO are as defined for Formula IV.

For chemically-enhanced primers of Formula VI-A, LINKER has a structure of the following formula:

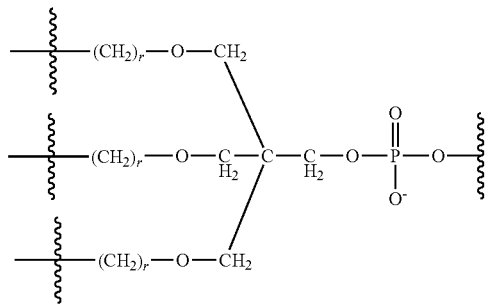

In the group of chemically-enhanced primers of Formula VI-A, one exemplary sub-group has a structure of Formula VI-A1:

Formula VI-A1

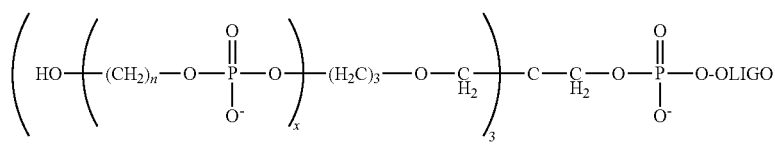

wherein n, x and OLIGO are as defined for Formula IV.

The chemically-enhanced primer of Formula VI-A may have any combination of B, n, r, x, m, y, z, K or W of the ranges and selections disclosed above for Formula IV, Formula VI, and Formula VI-A.

Figures 1A, 1B:
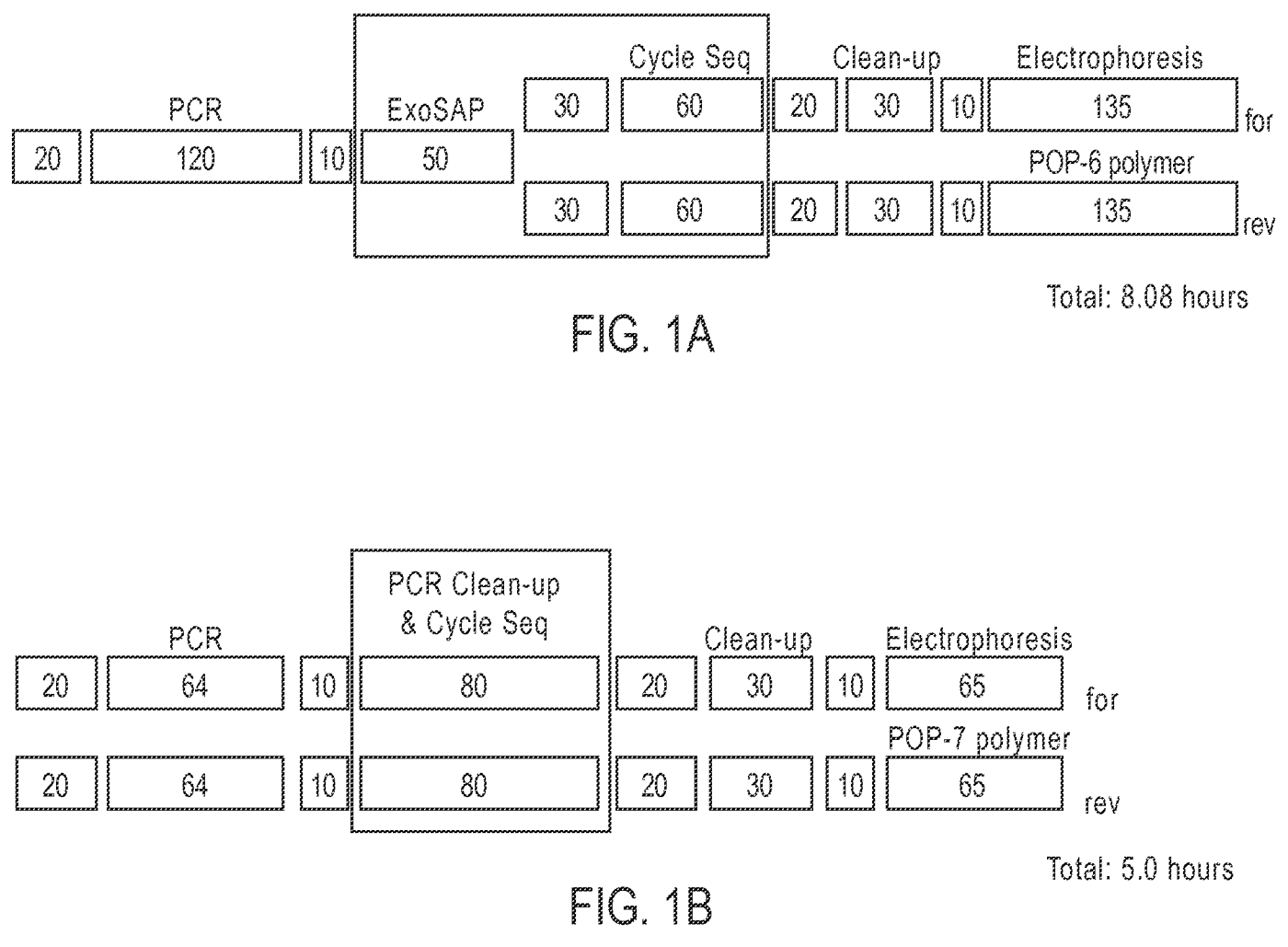

Using the chemically-enhanced sequencing primer, it has been found that high quality and highly accurate nucleic acid sequence results can be obtained in about 50% less time overall for a PCR to sequencing results workflow using POP7™ polymer on any of the 3130, 3730 or 3500 capillary electrophoresis platforms (Applied Biosystems, Foster City, Calif.) and with results comparable to the slower POP6™ polymer (Compare FIGS. 1A and 1B). Specifically, improvement of 5' sequence resolution to base 1 from the chemically-enhanced sequencing primer. Prior to the present teachings a standard sequencing primer using the BigDye® Terminator Kit v3.1 (Applied Biosystems) with POP-7™ polymer did not provided interpretable data the first 20-30 bases after the sequencing primer while using the POP-6™ polymer and BigDye® Terminator Kit v1.1 was able to obtain readable sequence by capillary electrophoresis within five bases of the sequencing primer, yet the throughput time with POP-6 polymer is slower (data not shown). The current teachings provide a NCM sequencing primer that provided high quality bases right after the sequencing primer with POP-7™ polymer by capillary electrophoresis and with resolution typically equivalent or superior in quality to BigDye® Terminator v1.1 with POP-6™ polymer (see FIG. 3 of U.S. Ser. No. 61/407,899, filed Oct. 28, 2011 and U.S. Ser. No. 61/408,553, filed Oct. 29, 2011). The chemically-enhanced sequencing primer is able to run with POP-7 polymer having an electrophoretic run time as short as 65 minutes to generate 700 high quality bases starting from the first base using a 3500 Genetic Analyzer (Applied Biosystems)(FIG. 1B). In contrast, it took 135 minutes with POP-6 polymer to produce only 600 high quality bases (FIG. 1A). The primer of the present teachings in conjunction with the POP-7 polymer provided a 52% throughput increase compared to the electrophoresis time with the POP-6 polymer. The throughput was increased as well as reducing hands-on-time by eliminating a separate PCR clean-up step prior to initiation of the sequencing reaction. (FIG. 1A and FIG. 1B). Overall, it can be seen that amplification, PCR clean-up and sequencing detection steps can each provide savings in run time, using differing aspects of the chemically-enhanced primers. The nuclease resistant aspect of the chemically-enhanced primers may provide reduced amplification and PCR clean-up time requirements, and the NCM aspect of the primers may allow efficacious separation in shorter run times, than standard sequencing primers can provide.

As shown in FIGS. 13-16 (presented in U.S. Ser. No. 61/407,899, filed Oct. 28, 2011 and U.S. Ser. No. 61/408,553, filed Oct. 29, 2011), the chemically-enhanced sequencing primer and workflow was used to investigate polymorphisms in Human Leukocyte Antigens (HLA). The HLAs are used for tissue and organ typing as well as tissue and organ cross-matching for transplantation matching and evaluation of rejection. The SeCore® HLA-DRB1 (Invitrogen, Carlsbad, Calif.) primer set and group specific sequencing primers (GSSP) were used on 34 DNA samples. Sequencing reactions were performed with traditional sequencing primers and with the chemically-enhanced sequencing primers. The sequencing reaction products were electrophoressed on an Applied Biosystems 3500xl™ Genetic Analyzer using POP7 polymer (Applied Biosystems). Comparison of 5' resolution and basecalling accuracy and quality was made between the two primers. On average the traditional sequencing primers with POP7 polymer yielded high quality readable bases by 25 bases after the sequencing primer while the chemically-enhanced sequencing primers yielded high quality bases by base 5 and by base 1 in many cases and also resulted in increased basecalling accuracy and a 40% decrease in overall workflow time. Table 1 provides examples of the improved sequencing quality obtained with the chemically-enhanced primers.

TABLE 1

| | Sample ID | allele 1 DNA | allele 2 DNA | # of edits BigDye ® Direct | # of edits Secore |
|---|---|---|---|---|---|
| 1 | D062 | DRB1*030101 | DRB1*0404 | 0 | 0 |
| 2 | D075 | DRB1*030101 | DRB1*100101 | 0 | 0 |
| 3 | D111 | DRB1*010101 | DRB1*080101 | 0 | 0 |
| 4 | D115 | DRB1*030101 | DRB1*1503 | 2 | 0 |
| 5 | D125 | DRB1*010101 | DRB1*070101 | 0 | 0 |
| 6 | D140 | DRB1*070101 | DRB1*1311 | 0 | 0 |
| 7 | D165 | DRB1*110101 | DRB1*1504 | 0 | 2 |
| 8 | D205 | DRB1*010201 | DRB1*1202 | 0 | 0 |
| 9 | D218 | DRB1*1001 | DRB1*1320 | 1 | 0 |
| 1 | D099 | DQB1*030101 | DQB1*050101 | 4 | 8 |
| 2 | D108 | DQB1*050101 | DQB1*0202 | 0 | 0 |
| 3 | D113 | DQB1*0201 | DQB1*050101 | 2 | 1 |
| 4 | D116 | DQB1*050301 | DQB1*060101 | 0 | 0 |
| 5 | D130 | DQB1*030302 | DQB1*0502 | 2 | 2 |
| 6 | D130 | DQB1*030302 | DQB1*0502 | 0 | 0 |
| 7 | D135 | DQB1*0202 | DQB1*030101 | 0 | 0 |
| 8 | D150 | DQB1*050201 | DQB1*030201 | 1 | 0 |
| 9 | D154 | DQB1*040102 | DQB1*060101 | 0 | 1 |
| 10 | D161 | DQB1*0201 | DQB1*0302 | 0 | 0 |
| 11 | D168 | DQB1*030101 | DQB1*050101 | 2 | 3 |
| 12 | D181 | DQB1*0301 | DQB1*0501 | 2 | 3 |
| 13 | F2150 | DQB1*0401/02 | DQB1*060101 . . . | 0 | 0 |
| 14 | F2160 | DQB1*0401/02 | 0DQB1*060101-17 | 0 | 1 |
| 15 | F2297 | DQB1*020101-04 . . . | DQB1*060101 | 0 | 2 |
| 16 | U415 | DQB1*0402 | DQB1*0601 | 0 | 0 |
| 17 | U415 | DQB1*0402 | DQB1*0601 | 1 | 1 |
| 1 | D049 | DPB1*010101 | DPB1*040101 | 0 | 0 |
| 2 | D105 | DPB1*110101 | DPB1*1701 | 0 | 0 |
| 3 | D149 | DPB1*1001 | DPB1*200101 | 0 | 0 |
| 4 | D157 | DPB1*010101 | DPB1*040101 | 0 | 0 |
| 5 | D161 | DPB1*040101 | DPB1*0601 | 0 | 0 |
| 6 | D164 | DPB1*020102 | DPB1*0601 | 0 | 0 |
| 7 | D219 | DPB1*040101 | DPB1*0501 | 0 | 0 |
| 8 | U514 | DPB1*0201 | DPB1*0401 | 0 | 0 |
| | | | total edits | 17 | 24 |

The results in Table 1 illustrate the relative basecalling accuracy between the SeCore® HLA Sequence and the chemically-enhanced sequencing primer when sequenced in both directions of exon 2 from HLA-DRB1, DQB1 and DPB1 in 34 different samples. uTYPE® HLA Sequencing Software (Invitrogen) aligned the forward and reverse traces to a reference sequence and a HLA library. Basecalling accuracy was assessed by how many base positions required manual edits to resolve discrepancies between the forward, reverse and reference sequence. The chemically-enhanced sequencing primer equaled or slightly outperformed the existing method by requiring fewer manual edits (17) and provided a simplified workflow and faster electrophoresis time vs. 24 edits with the traditional primers, method and workflow. The chemically-enhanced sequencing primer also improved 5' mobility seen as 5' C/A and A/G in DPB1, resolved shoulder problems in HLA-DQB1, and reduced C nucleotide compression routinely observed in HLA-DRB-1 sequences to substantially improve primary mixed basecalling (data not shown). The chemically-enhanced sequencing primer and improved workflow improved polymorphism detection and more efficient use of allele specific sequencing primers for heterozygous ambiguity resolution resulting in significant time savings for obtaining data that was superior in quality to existing methods.

According to various embodiments of the present teachings, a composition for sequencing nucleic acid can comprise a polymerase, a nuclease, a chemically-enhanced sequencing primer, dNTPs, and a chain terminator (e.g., ddNTPs). In some embodiments, the composition for sequencing nucleic acids can further comprise more than one chemically-enhanced sequencing primer. In some embodiments, the polymerase can comprise Taq polymerase, for example AmpliTaq Gold polymerase. In some embodiments, the nuclease can comprise exonuclease I. In some embodiments, the chemically-enhanced sequencing primer can comprise at least one phosphorothioate linkage. In other embodiments, the chemically-enhanced sequencing primer can comprise a terminal 3' end phosphorothioate linkage. In some embodiments, the ddNTPs can comprise ddNTPs-dyes, for example fluorescent dye-labeled ddNTPs. In some embodiments the chemically-enhanced sequencing primer can comprise a dye, for example a fluorescent dye-labeled oliogonucleotide and/or at least one fluorescently dye-labeled NCM moiety within the NCM compound.

According to various embodiments, the composition for sequencing nucleic acid can comprise a polymerase, for example a DNA polymerase, in an amount of from about 0.01 Unit to about 20 Units, for example, from about 0.1 Unit to about 1.0 Unit, or about 0.8 Unit. The composition can comprise polymerase in an amount within a range having an upper limit of from about 10 Units to about 20 Units and a lower limit of from about 0.01 Unit to about 0.05 Unit. According to various embodiments, the composition can comprise a nuclease, for example exonuclease I, in an amount of from about 1 Unit to about 40 Units, for example, from about 2 Units to about 15 Units, or about 10 Units. The composition can comprise nuclease in an amount within a range having an upper limit of from about 10 Units to about 40 Units, and a lower limit of from about 1 Unit to about 2 Units.

According to various embodiments, the composition for sequencing nucleic acid can comprise a chemically-enhanced sequencing primer, in an amount of from about 0.1 µM to about 20 µM, for example about 1.0 µM. The composition can comprise a chemically-enhanced sequencing primer in an amount within a range having an upper limit of from about 10 µM to about 20 µM and a lower limit of from about 0.05 µM to about 0.1 µM. According to various embodiments, the composition can comprise dNTPs in an amount of from about 20 µM to about 5000 µM, for example, about 500 µM. The composition can comprise dNTPs in an amount within a range having an upper limit of from about 2000 µM to about 5000 µM and a lower limit of from about 20 µM to about 50 µM. According to various embodiments, the composition can comprise ddNTPs in an amount of from about 0.03 µM to about 10 µM, for example about 3 µM. The composition can comprise ddNTPs in an amount within a range having an upper limit of from about 5 µM to about 10 µM and a lower limit of from about 0.01 µM to about 0.05 µM. All molar amounts are based on final concentrations of the final volume.

According to various embodiments, the composition can comprise a non-nuclease-resistant amplification primer in an amount of from about 0.1 µM to about 20 µM, for example about 1.0 µM. The composition can comprise a non-nuclease-resistant amplification primer in an amount within a range having an upper limit of from about 10 µM to about 20 µM and a lower limit of from about 0.05 µM to about 0.1 µM. All molar amounts are based on final concentrations of the final volume.

According to various embodiments, the composition for sequencing nucleic acid can further comprise a PCR amplification product. In some embodiments, the PCR amplification product can comprise an amplified DNA target sequence. In some embodiments, the PCR amplification product can comprise non-nuclease-resistant amplification primer(s). The non-nuclease-resistant amplification primer can comprise, for example, phosphodiester linkages that are sensitive to degradation by exonuclease. In some embodiments, the PCR amplification product can comprise a target specific amplicon that incorporates nucleic acid sequence capable of annealing to a universal primer.

According to various embodiments of the present teachings, a method of preparing a nucleic acid for sequencing can comprise a step of amplifying the nucleic acid under conditions to produce amplification reaction products. The nucleic acid can be amplified using, for example, polymerase chain reaction (PCR). The nucleic acid can also be amplified using other methods such as, for example, multiple strand displacement amplification, helicase displacement amplification, nick translation, Q beta replicase amplification, rolling circle amplification, and other isothermal amplification methods.

According to various embodiments, the nucleic acid to be amplified can comprise, for example, RNA, DNA, cDNA, genomic DNA, viral DNA, plasmid DNA, recombinant DNA, amplicon DNA, synthetic DNA or the like. Template molecules can be obtained from any of a variety of sources. For example, DNA as a template molecule can be isolated from a sample, which can be obtained or derived from a subject. The word "sample" is used in a broad sense to denote any source of a template on which sequence determination is to be performed. The phrase "derived from" is used to indicate that a sample and/or nucleic acids in a sample obtained directly from a subject comprising nucleic acid can be further processed to obtain template molecules.

The source of a sample can be of any viral, prokaryotic, archaebacterial, or eukaryotic species or a synthetic species. In certain embodiments the source can be a human. The sample can comprise, for example, embryonic, cultured cells, tissues or organs, bone, tooth, organ, tissue, preserved, e.g., formalin-fixed paraffin embed (PFPE) organ or tissue, degraded, mummified, or tissue including blood or another body fluid containing cells, such as sperm, a biopsy sample, or the like. Mixtures of nucleic acids from different samples and/or subjects can be combined. Samples can be processed in any of a variety of ways. Nucleic acids can be isolated, purified, and/or amplified from a sample using known methods.

Amplifying nucleic acid can typically result in a reaction product that comprises excess amplification primer and an amplicon (also referred to as an amplification product) that comprises a target nucleic acid. According to various embodiments, a method of preparing nucleic acid for sequencing can comprise removing excess amplification primer from the reaction product. In some embodiments, the amplification primer can be removed, for example, by adding a nuclease enzyme and providing appropriate conditions for the nuclease to degrade the amplification primer. In some embodiments, the amplification primer can be removed by contacting the amplification reaction product with a reaction mixture comprising a nuclease enzyme. Nucleases suitable for use in the subject methods preferentially degrade single-stranded polynucleotides over double-stranded polynucleotides, thus destroying excess primers while leaving intact double-stranded amplicons available for sequencing in subsequent steps. In various embodiments, the nuclease enzyme can comprise, for example, exonuclease I. Exonuclease I can be obtained from various commercial suppliers, for example from USB Corp., Cleveland, Ohio. Appropriate reaction conditions can include, for example, optimal time, temperature, and buffer parameters to provide for nuclease enzyme activity. In some embodiments, for example, excess amplification primer can be degraded by adding exonuclease I to the amplification reaction product and incubating at about 37° C. for about 10 to about 30 min. Exonuclease I can hydrolyze single-stranded DNA in a 3'→5' direction.

According to various embodiments of a method for preparing a nucleic acid, a reaction mixture can further comprise a chemically-enhanced sequencing primer. The chemically-enhanced sequencing primer can be essentially non-degraded by a reaction mixture comprising a nuclease, for example, exonuclease I, under reaction conditions at which excess amplification primer can be degraded by the nuclease. By "essentially non-degraded" it is intended that any degradation that takes place of the chemically-enhanced sequencing primer is not of a level that significantly interferes with the process employed to generate sequencing and/or fragment analysis data in the subsequent sequencing reactions or fragment analysis reactions.

According to various embodiments, the chemically-enhanced sequencing primer can comprise an oligonucleotide sequence. In some embodiments, the chemically-enhanced sequencing primer can comprise one of more nuclease-resistant internucleotide linkage(s). For example, the internucleotide linkage may be a phosphorothioate linkage. In some embodiments, the chemically-enhanced sequencing primer can comprise a nuclease-resistant internucleotide linkage at a terminal 3' end, at a terminal 5' end, and/or at one or more internal linkage sites. In some embodiments, the nuclease resistant internucleotide linkage is at least one phosphorothioate linkage. Chemically-enhanced sequencing primers were synthesized having one or two phosphorothioate linkages on the terminal 3' end to protect the chemically-enhanced sequencing primers from exonuclease I digestion. The Sp stereoisomer can protect the primer from exonuclease I digestion but the Rp stereoisomer was found to provide no protection from exonuclease I digestion (data not shown).

The use of a chemically-enhanced sequencing primer having the configuration $(C3)_8$-trebler-M13Rev with either one or two phosphorothioate linkages was evaluated in the sequencing of two templates, #30 and #122. It was found that in both templates the first base (A) is split into two peaks with the primer having one phosphorothioate linkage, and the first two bases (A and T) were split with the primer having two phosphorothioate linkages because the stereoisomers have slightly different mobilities. For the primer with one phosphorothioate linkage, there is either oligo-Sp or oligo-Rp. In the case of two phosphorothioate linkages on the terminal 3' end of the primer, there were four possible isomers (oligo-Sp-Sp, oligo-Rp-Sp, oligo-Rp-Rp and oligo-Sp-Rp) on the primer with two phosphorothioate linkages. It was found that as with plasmid sequencing, mobility differences were caused by the Sp and Rp stereoisomers resulted in the splitting of the first two peaks.

In some embodiments, the chemically-enhanced primer can comprise a negatively charged group/compound/molecule (NCM). For example, the NCM can be located at the terminal 5' end of the oligonucleotide sequence or within the oligonucleotide sequence. Examples of NCM are disclosed above (FIGS. 3A-3J, 4A-4C). The NCM can be attached to both a non-dye-labeled oligonucleotide sequence which functions as the primer sequence as well as to a dye-labeled oligonucleotide sequence which function as the primer sequence. In some embodiments, the dye can be attached to a nucleotide or nucleotide analog of the oligonucleotide sequence or to the NCM as would be known to one of skill in the art.

The movement of DNA fragments under an electric field depends on the charge to mass ratio. The DNA fragment can move differently by adding a NCM. Numerous NCM configurations and compositions attached to sequencing primers were evaluated for their ability to change the amplified sequencing fragments mobility under an electric field. FIGS. 3A-3J, 4A-4C illustrate exemplary M13 oligonucleotide sequence primers and gene-specific primers with various NCMs. The chromatograms illustrating the results of sequencing reactions with the exemplary NCM+oligonucleotide sequence primer structures with a variety of templates can be found in FIGS. 3-12 and 16 of U.S. Ser. No. 61/407,899, filed Oct. 28, 2011 and U.S. Ser. No. 61/408,553, filed Oct. 29, 2011).

In various embodiments, "analogs" in reference to nucleosides/tides and/or polynucleotides comprise synthetic analogs having modified nucleobase portions, modified pentose portions and/or modified phosphate portions, and in the case of polynucleotides, modified internucleotide linkages, as described generally elsewhere (e.g., Scheit, *Nucleotide Analogs* (John Wiley, New York, (1980); Englisch, *Angew. Chem. Int. ed. Engl.* 30:613-29 (1991); Agrawal, *Protocols for Polynucleotides and Analogs*, Humana Press (1994)). Generally, modified phosphate portions comprise analogs of phosphate wherein the phosphorous atom is in the +5 oxidation state and one or more of the oxygen atoms is replaced with a non-oxygen moiety e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Exemplary modified nucleobase portions include but are not limited to 2,6-diaminopurine, hypoxanthine, pseudouridine, C-5-propyne, isocytosine, isoguanine, 2-thiopyrimidine, and other like analogs. Particularly preferred nucleobase analogs are iso-C and iso-G nucleobase analogs available from Sulfonics, Inc., Alachua, Fla. (e.g., Benner, et al., U.S. Pat. No. 5,432,272). Exemplary modified pentose portions include but are not limited to 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, bromo and the like. Modified internucleotide linkages include phosphate analogs, analogs having achiral and uncharged intersubunit linkages (e.g., Sterchak, E. P., et al., Organic Chem, 52:4202 (1987)), and uncharged morpholino-based polymers having achiral intersubunit linkages (e.g., U.S. Pat. No. 5,034,506). A particularly preferred class of polynucleotide analogs where a conventional sugar and internucleotide linkage has been replaced with a 2-aminoethylglycine amide backbone polymer is peptide nucleic acid (PNA) (e.g., Nielsen et al., Science, 254:1497-1500 (1991); Egholm et al., J. Am. Chem. Soc., 114: 1895-1897 (1992)).

According to various embodiments, the chemically-enhanced primer can comprise a universal primer, selected from US1, M13, T7, SP6, T3, or other sequencing primers as would be known to one of skill in the art. For example, an M13 universal forward primer, an M13 universal reverse primer, or the like. In other embodiments, the chemically-enhanced primer can comprise an oligonucleotide sequence or a specific gene specific oligonucleotide sequence, to the target nucleic acid sequence for which the nucleic acid sequence was to be determined. A gene specific oligonucleotide sequence may be substantially hybridizable to a region of a target nucleic acid on either the 5' or 3' side of a locus of interest. The oligonucleotide primer sequence can be the identical primer sequence as the sequence of the amplification primer used to generate the PCR amplification product having the amplified nucleic acid target sequence and/or DNA target sequence.

In some embodiments, the chemically-enhanced primer may include an gene specific oligonucleotide sequence that is substantially hybridizable to a region of a target nucleic acid which encompasses a locus of interest.

While embodiments of a method for preparing nucleic acid for sequencing can comprise using a phosphorothioated sequencing primer, and the teachings disclosed herein exemplify using a sequence primer having a NCM at or near the terminal 5' end and a phosphorothioated terminal 3' end of an oligonucleotide sequence, other types of chemically-enhanced primers can be utilized within the scope of the present teachings. For example, a nuclease resistant sequencing primer can comprise an alkyl phosphonate monomer, RO—P(=O)(-Me)(—OR), such as dA-Me-phosphonamidite, and/or a triester monomer, RO—P(=O)(—OR')(—OR), such as dA-Me-phosphoramidite (available from Glen Research, Sterling, Va.), and/or a locked nucleic acid monomer (available from Exiqon, Woburn, Mass.), and/or a boranophosphate monomer, RO—P(—BH$_3$)(=O)(—OR), as described by Shaw, Barbara Ramsey, et al., in "Synthesis of Boron-Containing ADP and GDP Analogues: Nucleoside 5'-(P-Boranodisphosphates)", Perspectives in Nucleoside and Nucleic Acid Chemistry, pg. 125-130, (2000), or the like.

According to various embodiments, the amplification reaction products can comprise a target amplicon. In some embodiments, the target amplicon can comprise a result of PCR amplification from amplification primers. In some embodiments, the target amplicon can comprise double stranded DNA. In some embodiments, the target amplicon can comprise single stranded DNA.

According to various embodiments, the amplification primers can comprise tailed primers. The tailed primers can be used, for example, to generate a target specific amplicon that incorporates nucleic acid sequence capable of annealing to a universal primer or a gene specific primer.

According to various embodiments, a method for preparing nucleic acid for sequencing can comprise inactivating a nuclease after excess primer is degraded by the nuclease. In some embodiments, the nuclease can be inactivated by heating. For example, the nuclease can be heat-inactivated by heating to a temperature of from about 80° C. to about 90° C. for about 15 minutes. In various embodiments, the inactivation of the nuclease can occur within the vesicle and in the same reaction step as the sequencing reaction as shown in FIG. 1B in the Cycle Seq. (cycle sequencing) step.

According to various embodiments of the present teachings, templates to be sequenced can be synthesized by PCR in individual aqueous compartments (also called "reactors") of an emulsion. In some embodiments, the compartments can each contain a particulate support such as a bead having a suitable first amplification primer attached thereto, a first copy of the template, a second amplification primer, and components needed for a PCR reaction (for example nucleotides, polymerase, cofactors, and the like). Methods for preparing emulsions are described, for example, in U.S. Pat. No. 6,489,103 B1, U.S. Pat. No. 5,830,663, and in U.S. Patent Application Publication No. US 2004/0253731. Methods for performing PCR within individual compartments of an emulsion to produce clonal populations of templates attached to microparticles are described, for example, in Dressman, D., et al, Proc. Natl. Acad. Sci., 100(15):8817-8822, 2003, and in PCT publication WO2005010145. All of the patents, applications, publications, and articles described herein are incorporated in their entireties by reference.

According to various embodiments, a method for sequencing nucleic acid can comprise amplifying nucleic acid in a first reaction mixture comprising nuclease sensitive amplification primers to form amplified nucleic acid, contacting the first reaction mixture with a second reaction mixture comprising a nuclease and a chemically-enhanced primer, under conditions in which the nuclease sensitive amplification primers are degraded by the nuclease, and inactivating the nuclease and causing the amplified nucleic acid to react in a sequencing reaction under conditions in which the chemically-enhanced primer primes the sequencing reaction. According to various embodiments, results can be obtained based on the sequencing reaction and a nucleotide base sequence of the amplified nucleic acid can be determined based on the results. According to various embodiments, the nucleotide base sequence can be determined by a mobility-dependent separation of the sequencing reaction products. According to various embodiments, the amplifying can be by polymerase chain reaction amplification.

According to various embodiments, the second reaction mixture can further comprise dNTPs, ddNTPs, a dye-label, and a thermo-stable DNA polymerase. In some embodiments, each of the ddNTPs can be labeled with a different fluorescent dye (ddNTP-dye). For example, the ddNTPs can comprise BigDye ddNTPs, available from Applied Biosystems, Foster City, Calif. In some embodiments, the chemically-enhanced primer can be labeled with a fluorescent dye. The label can be attached to the oligonucleotide sequence and/or the NCM region of the chemically-enhanced primer. The thermo-stable DNA polymerase can comprise, for example, a DNA polymerase known to one of skill in the art. In some embodiments, the sequencing reaction can comprise a thermal cycle sequencing reaction.

In other embodiments, the chemically-enhanced primers can be utilized in a sequencing reaction performed without an initial amplification step. Such sequencing methods may sequence either single or doubled stranded nucleic acids. For example, plasmid sequencing may be more efficiently performed using one or both of a primer pair having the structure of a chemically-enhanced primer as disclosed herein. In some embodiments, a chemically-enhanced primer may have inter-nucleotide linkages that are all phosphodiester linkages. In other embodiments of plasmid sequencing methods, a chemically-enhanced primer may have at least one phosphothiorate inter-nucleotide linkage. In some embodiments, the chemically-enhanced primer has one phosphothioate linkage.

In another method, one or more chemically-enhanced primers may be used for ligation extension reactions. In some embodiments, the chemically-enhanced primer for use in a ligation extension reaction is labeled fluorescently. In some embodiments, the ligation extension chemically-enhanced primer is labeled fluorescently at a 3' terminus.

A variety of nucleic acid polymerases may be used in the methods described herein. For example, the nucleic acid polymerizing enzyme can be a thermostable polymerase or a thermally degradable polymerase. Suitable thermostable polymerases include, but are not limited to, polymerases isolated from *Thermus aquaticus, Thermus thermophilus, Pyrococcus woesei, Pyrococcus furiosus, Thermococcus litoralis,* and *Thermotoga maritima.* Suitable thermodegradable polymerases include, but are not limited to, *E. coli* DNA polymerase I, the Klenow fragment of *E. coli* DNA polymerase I, T4 DNA polymerase, T5 DNA polymerase, T7 DNA polymerase, and others. Examples of other polymerizing enzymes that can be used in the methods described herein include T7, T3, SP6 RNA polymerases and AMV, M-MLV and HIV reverse transcriptases.

Non-limiting examples of commercially available polymerases that can be used in the methods described herein include, but are not limited to, TaqFS®, AmpliTaq® CS (Applied Biosystems), AmpliTaq FS (Applied Biosystems), AmpliTaq Gold® (Applied Biosystems), Kentaq1 (AB Peptide, St. Louis, Mo.), Taquenase (ScienTech Corp., St. Louis, Mo.), ThermoSequenase (Amersham), Bst polymerase, Vent$_R$(exo⁻) DNA polymerase, Reader™ Taq DNA polymerase, VENT™ DNA polymerase (New England Biolabs), DEEP-VENT™ DNA polymerase (New England Biolabs), PFU-Turbo™ DNA polymerase (Stratagene), Tth DNA polymerase, KlenTaq-1 polymerase, SEQUENASE™ 1.0 DNA polymerase (Amersham Biosciences), and SEQUENASE 2.0 DNA polymerase (United States Biochemicals).

According to various embodiments of a method for sequencing nucleic acid, the nuclease can comprise exonuclease I. The exonuclease I can be sensitive to heat inactivation and can be essentially 100 percent deactivated by heating, for example, heating at about 80° C. for about 15 minutes. Other heat inactivated nucleases may be used in the subject methods and compositions including but not limited to Exo III, Pfu or DNA pol I.

According to various embodiments, the chemically-enhanced primer comprises at least one phosphorothioate linkage. In some embodiments, the chemically-enhanced primer comprises at least one terminal 3' end phosphorothioate linkage. In some embodiments, as described above, the chemically-enhanced primer comprises a NCM and an oligonucleotide sequence 5' of the phosphorothioate linkage.

The sequencing reaction products can be analyzed on a sieving or non-sieving medium. In some embodiments of these teachings, for example, the PCR products can be analyzed by electrophoresis; e.g., capillary electrophoresis, as described in H. Wenz et al. (1998), GENOME RES. 8:69-80 (see also E. Buel et al. (1998), J. FORENSIC SCI. 43:(1), pp. 164-170)), or slab gel electrophoresis, as described in M. Christensen et al. (1999), SCAND. J. CLIN. LAB. INVEST. 59(3): 167-177, or denaturing polyacrylamide gel electrophoresis (see, e.g., J. Sambrook et al. (1989), in MOLECULAR CLONING: A LABORATORY MANUAL, SECOND EDITION, Cold Spring Harbor Laboratory Press, Cold Spring Harbor, N.Y., pp. 13.45-13.57). The separation of DNA fragments in electrophoresis is based primarily on differential fragment size. Sequencing reaction products can also be analyzed by chromatography; e.g., by size exclusion chromatography (SEC). Likewise, fragment analysis can be carried in a similar manner as would be known to the skilled artisan.

According to various embodiments a system for sequencing DNA can comprise amplifying DNA in a first reaction mixture comprising nuclease sensitive amplification primers to form amplified DNA; contacting said first reaction mixture of the amplifying step with a second reaction mixture comprising a nuclease and a chemically-enhanced primer, under conditions in which the nuclease sensitive amplification primers are degraded by the nuclease; inactivating the nuclease and causing the amplified DNA to react in a sequencing reaction under conditions in which the chemically-enhanced primer primes said sequencing reaction; and identifying a nucleotide base sequence of the amplified DNA by mobility-dependent separation of sequencing reaction products. In various embodiments, the system for sequencing DNA, the mobility-dependent separation is selected from separation by charge and separation by size, wherein the separation by size plus charge is selected from gel electrophoresis and capillary electrophoresis and separation by size is by a liquid gradient, and a denaturing gradient medium.

The present teachings are also directed to kits that utilize the chemically-enhanced primer composition and methods described above. In some embodiments, a basic kit can comprise a container having one or more chemically-enhanced primers. A kit can also optionally comprise instructions for use. A kit can also comprise other optional kit components, such as, for example, one or more of a nuclease, a sufficient quantity of enzyme for sequencing or fragment analysis, buffer to facilitate the sequencing reaction or fragment analysis reaction, dNTPs, modified dNTPs, dNTP analogs and 7-Deaza-dGTP for strand extension during sequencing reaction or fragment analysis reaction, ddNTPs, a dye-label, loading solution for preparation of the sequenced or fragment analyzed material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated detectors or analyzers. Kits may have more than one chemically enhanced primer, and the number of NCM moieties may be different in each of the chemically enhanced primers. Kits for plasmid sequencing may have any of the components listed above, but do not include a nuclease.

Examples of the compositions and methods of the present teachings are shown below. These examples are not limiting of the present teachings, and those of ordinary skill in the art will recognize that the components used in the reactions may be readily substituted with equivalent reagents known in the art.

The following Examples illustrate the ability of the chemically-enhanced primer to provide higher resolution of a sequencing reaction and in less time with POP7 polymer and variants thereof, the stability of the chemically-enhanced primer to exonuclease I, the incorporation of the chemically-enhanced primer as a substrate for DNA polymerase, the compatibility of exonuclease I with the sequencing reagents, and the susceptibility of non-phosphorothioate primer to exonuclease I digestion. The Examples further illustrate the use of tailed amplification primers along with universal phosphorothioate primers for sequencing.

Example 1

C6 Spacer+Olio Seq. Synthesis, No Phosphorothioate Group

An 18 base oligonucleotide labeled with one or more C6 spacers at the 5' position was made on an ABI model 394 DNA synthesizer using standard phosphoramidite chemistry. The C6 spacer phosphoramidite was obtained from Chem Genes Corp. (P/N CLP-1120, Wilmington, Mass.). The labeled 18 mer was made with the trityl group intact from a one micromole column. On completion of the synthesis the oligonucleotide was cleaved off the support with NH$_4$OH and purified by HPLC using an ABI RP-300 (C-8) column (4.6×220 mm) using a flow rate of 1.5 ml/min. and a solvent gradient of 0.1M triethylammonium acetate-water pH 7.0 and acetonitrile, the trityl group was removed and the product was isolated by ethanol precipitation.

C3 Spacer+Oligo Seq. Synthesis, No Phosphorothioate Group:

An 18 base oligonucleotide labeled with one or more C3 spacers (P/N 10-1913-90, Glen Research), at the 5' position was made on an ABI model 394 DNA synthesizer using standard phosphoramidite chemistry. The labeled 18 mer was made with the trityl group intact from a one micromole column. On completion of the synthesis the oligonucleotide was cleaved off the support with NH$_4$OH and purified by HPLC using an ABI RP-300 (C-8) column (4.6×220 mm)

using a flow rate of 1.5 ml/min. and a solvent gradient of 0.1M triethylammonium acetate-water pH 7.0 and acetonitrile, the trityl group was removed and the product was isolated by ethanol precipitation.

Protocol for Oligo Labeled with a 5' Phosphate:

An 18 base oligonucleotide labeled with a phosphate group at the 5' position. This was made on an ABI model 394 DNA synthesizer using standard phosphoramidite chemistry. The phosphate group was generated using a phosphoramidite obtained from Glen Research (P/N 10-1922-90) The labeled 18 mer was made from a one micromole column and on completion of the synthesis the oligonucleotide was cleaved off the support with $NH_4OH$ and purified by HPLC using an ABI RP-300 (C-18) column (4.6×220 mm) using a flow rate of 1.5 ml/min. and a solvent gradient of 0.1M triethylammonium acetate-water pH 7.0 and acetonitrile. The product was then isolated by ethanol precipitation.

Protocol for Oligo Labeled with Dual Branching (Doubler) Linker Labeled with One or More C3 Spacers:

An 18 base oligonucleotide labeled with a dual branching linkage followed by one or more C3 spacers at the 5' position was made on an ABI model 394 DNA synthesizer using standard phosphoramidite chemistry. The dual (doubler) branching (P/N 10-1920-90) and C3 spacer (P/N 10-1913-90) phosphoramidites were obtained from Glen Research. The labeled 18 mer was made with the trityl group intact using a one micromole synthesis column. On completion of the synthesis the oligonucleotide was cleaved off the support with $NH_{400}H$ and purified by HPLC using an ABI RP-300 (C-18) column (4.6×220 mm) using a flow rate of 1.5 ml/min. and a solvent gradient of 0.1M triethylammonium acetate-water pH 7.0 and acetonitrile, the trityl group was removed and the product was isolated by ethanol precipitation.

Protocol for Olio Labeled with Trebler Branching (Trebler) Linker Labeled with One or More C3 Spacers:

An 18 base oligonucleotide labeled with a trebler branching linkage followed by one or more C-3 spacers at the 5' position was made on an ABI model 394 DNA synthesizer using standard phosphoramidite chemistry. The trebler phosphoramidite (P/N 10-1922-90) and C-3 spacer (P/N 10-1913-90) phosphoramidites were obtained from Glen Research. The labeled 18 mer was made with the trityl group intact using a one micromole synthesis column. On completion of the synthesis the oligonucleotide was cleaved off the support with $NH_4OH$ and purified by HPLC using an ABI RP-300 (C-18) column (4.6×220 mm) using a flow rate of 1.5 ml/min. and a solvent gradient of 0.1M triethylammonium acetate-water pH 7.0 and acetonitrile, the trityl group was removed and the product was isolated by ethanol precipitation.

Protocol for Oligo Labeled with Trebler Branching Linker End Labeled with Phosphates (3 Total Phosphates):

An 18 base oligonucleotide labeled with a trebler branching linkage at the 5' position followed by phosphorylation was made on an ABI model 394 DNA synthesizer using standard phosphoramidite chemistry. The trebler branching (P/N 10-1922-90) and phosphorylating (P/N 10-1900-90) phosphoramidites were obtained from Glen Research. The labeled 18 mer was made using a one micromole synthesis column. On completion of the synthesis the oligonucleotide was cleaved off the support with $NH_4OH$ and purified by HPLC using an ABI RP-300 (C-18) column (4.6×220 mm) using a flow rate of 1.5 ml/min. and a solvent gradient of 0.1M triethylammonium acetate-water pH 7.0 and acetonitrile. The product was isolated by ethanol precipitation.

Protocol for Oligo Labeled with Two Generations of Trebler Branching Linker End Labeled with Phosphates (9 Total Phosphates):

An 18 base oligonucleotide labeled with 2 additions of trebler branching linkages at the 5' position followed by phosphorylation was made on an ABI model 394 DNA synthesizer using standard phosphoramidite chemistry. The trebler branching (P/N 10-1922-90) and phosphorylating (P/N 10-1900-90) phosphoramidites were obtained from Glen Research. The labeled 18 mer was made using a one micromole synthesis column. On completion of the synthesis the oligonucleotide was cleaved off the support with $NH_4OH$ and purified by HPLC using an ABI RP-300 (C-18) column (4.6×220 mm) using a flow rate of 1.5 ml/min. and a solvent gradient of 0.1M triethylammonium acetate-water pH 7.0 and acetonitrile. The product was isolated by ethanol precipitation.

Protocol for Oligo Labeled with One or More C-3 Spacer Containing a 3' Phosphorothioate Linkage:

An 18 base oligonucleotide labeled with one or more C-3 spacers at the 5' position was made on an ABI model 394 DNA synthesizer using standard phosphoramidite chemistry. The 3' phosphorothioate linkage was made using standard methods with sulfurizing reagent (TETD P/N 401267 (Applied Biosystems, Foster City, Calif.). The C3 spacer phosphoramidite was obtained from Glen Research (P/N 10-1913-90). The labeled 18 mer was made with the trityl group intact from a one micromole synthesis column. On completion of the synthesis the oligonucleotide was cleaved off the support with $NH_4OH$ and purified by HPLC using an ABI RP-300 (C-18) column (4.6×220 mm) using a flow rate of 1.5 ml/min. and a solvent gradient of 0.1M triethylammonium acetate-water pH 7.0 and acetonitrile, the trityl group was removed and the product was isolated by ethanol precipitation. Note: To synthesize more than one phosphorothioate linkage or to place this linkage anywhere in the 18-mer oligonucleotide chain, oxidize using the sulfurizing reagent at these position(s).

Example 2

PCR and Sequencing Reactions:

PCR and Sequencing Reactions Using a Chemically-Enhanced Primer with a Terminal 3' Phosphorothioate (PS) Linkage PCR Amplification PCR reactions were carried out in the following 10 µL solution: to sequence amplicon RSA000013703, 1 µL 4 ng/µL gDNA, M13-tagged primers (0.8 uM each): 1.5 µL of TGTAAAACGACGGCCAGTTTGATGGGCTCAG-CAACAGGT (SEQ ID NO:1, gn|Probe|1292199b) and CAGGAAACAGCTATGACCCCACTGCTTGCGTTTCT-TCCTG (SEQ ID NO:2, gn|Probe|1292199c), 5 µL of BigDye Direct PCR Master Mix (P/N 4458699, Applied Biosystems) and 2.5 µL water. PCR was carried out on a Veriti™ 96-well thermal cycler (P/N 4375786, Applied Biosystems). with the following thermal cycling conditions: 95° C. for 10 minutes, then 35 cycles of 96° C. for 3 seconds, 62° C. for 15 seconds, and 68° C. for 30 sec. followed by 72° C. for 2 min. and 4° C. hold. To confirm amplification a 10 µL sample was analyzed on an agarose gel. A band consistent with the expected 626 bp amplicon was observed.

Amplicon RSA000013703 SEQ ID NO:3, template ZC is shown below with primer binding sites for PCR forward primer, and PCR reverse primer (reverse complement) underlined.

```
CAGGAAACAGCTATGACCCCACTGCTTGCGTTTCTTCCTGTTTTAAT

CCCACTTTCAATGAAGTGTGTATTTGAAATAAATGGCTCATGAGTTA

ATCACATCTTTATATATCCTAAGATGTATTACAAAGGCTTCCATAAC

ACTTGTCTATAGTAAGCCACTCATTTCTATAATTTTTCTTTCAATAA

ACTCAATCTTTGTAATACAGAAATTAACCTTCTGGGTTGTTTTTGTT

CAAGATCTTCAGTTTGATTTGCCCCTTGGTTGATCTGTTTTTCCCAT

CGCTGAACTGGTTCCCATAATCACACACCTTTGCTTTTCATTTCCAC

AGATCAAGGAATCAACATTTACCGAAAGCCACCCATCTACAAACAGC

ATGGTAAAACCCGCTTTCCTCCGCGTAGCTTTTAAATAGCAAAGTCA

GCTGAACTTCTCCTTGCTGTCCTCTGAAAGGCTTTTCCTGCTGCTGC

TTTTGAGAGTAAAACTGGGGCATCCAGCATATTATGCCTTTCTGGTC

TACTAAGATGTAAATATTGTAAAATTGATTCTCCTGGATGGAGAGAC

TTAGCTTGATTAGAAAGCTTCTAACCTGTTGCTGAGCCCATCAAACT

GGCCGTCGTTTTACA.
```

Figure 3A:
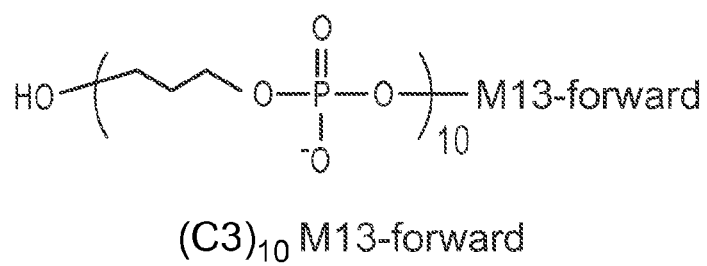
FIG. 3A illustrates a chemically-enhanced primer consisting of $(C3)_{10}$-M13*(Forward).
Figure 3B:
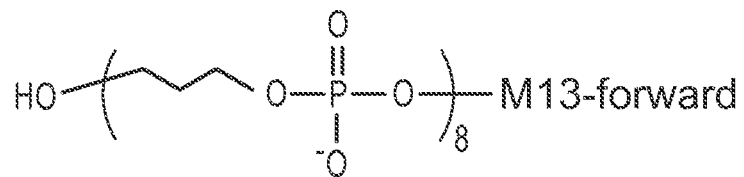
FIG. 3B illustrates a chemically-enhanced primer consisting of $(C3)_8$-M13 (Forward).
Figure 3C:
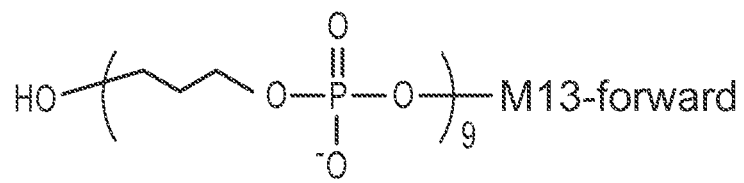
FIG. 3C illustrates a chemically-enhanced primer consisting of $(C3)_9$-M13 (Forward).
Figure 3D:
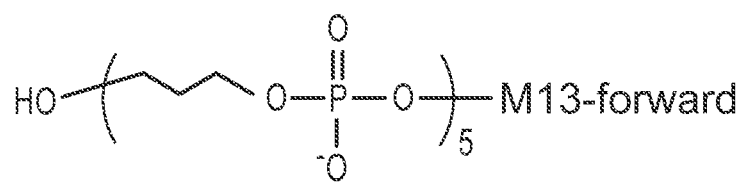
FIG. 3D illustrates a chemically-enhanced primer consisting of $(C3)_5$-M13 (Forward).
Figure 3E:
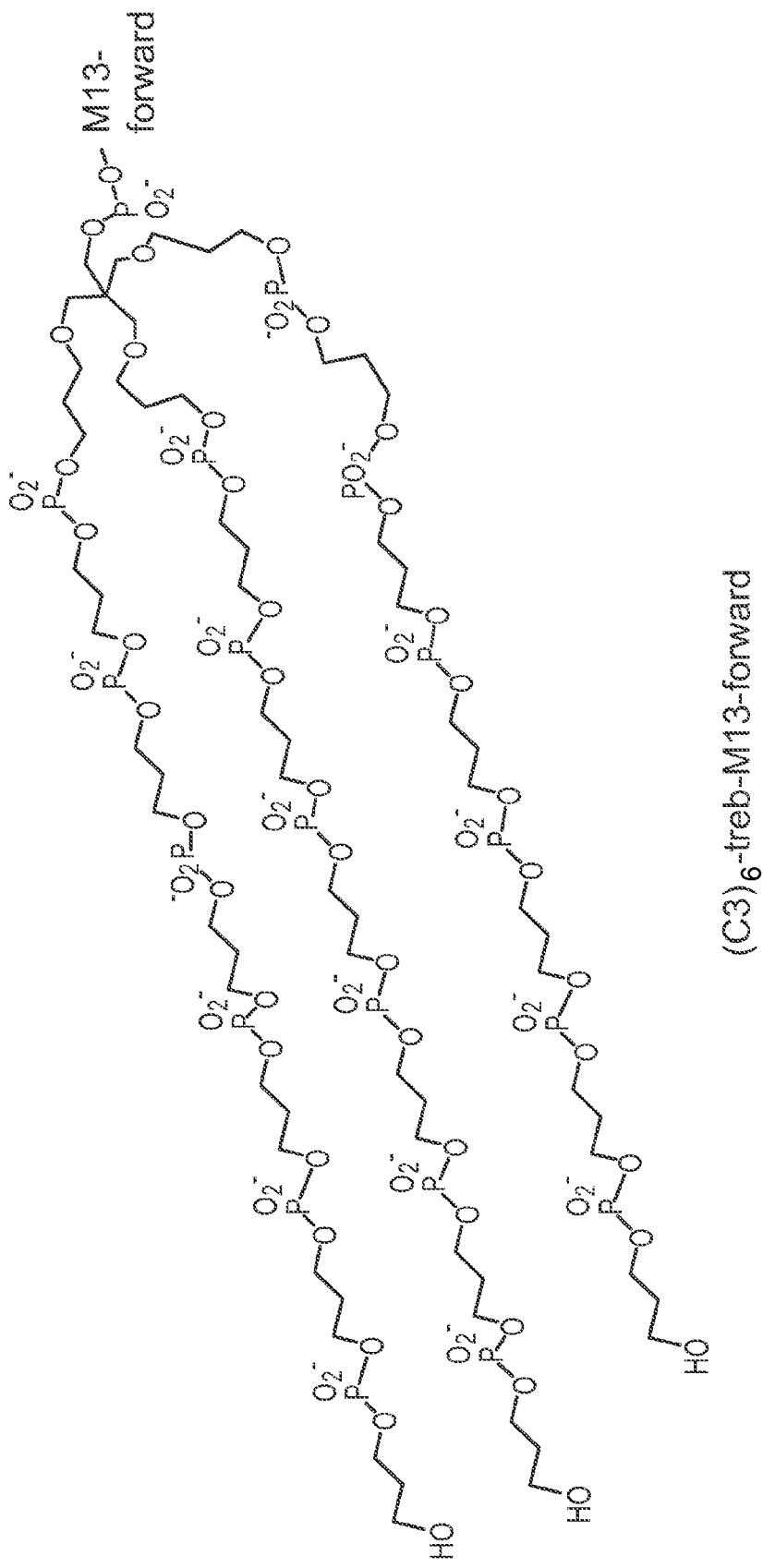
FIG. 3E illustrates a chemically-enhanced primer consisting of $(C3)_6$-trebler-M13 (Forward).
Figure 3F:
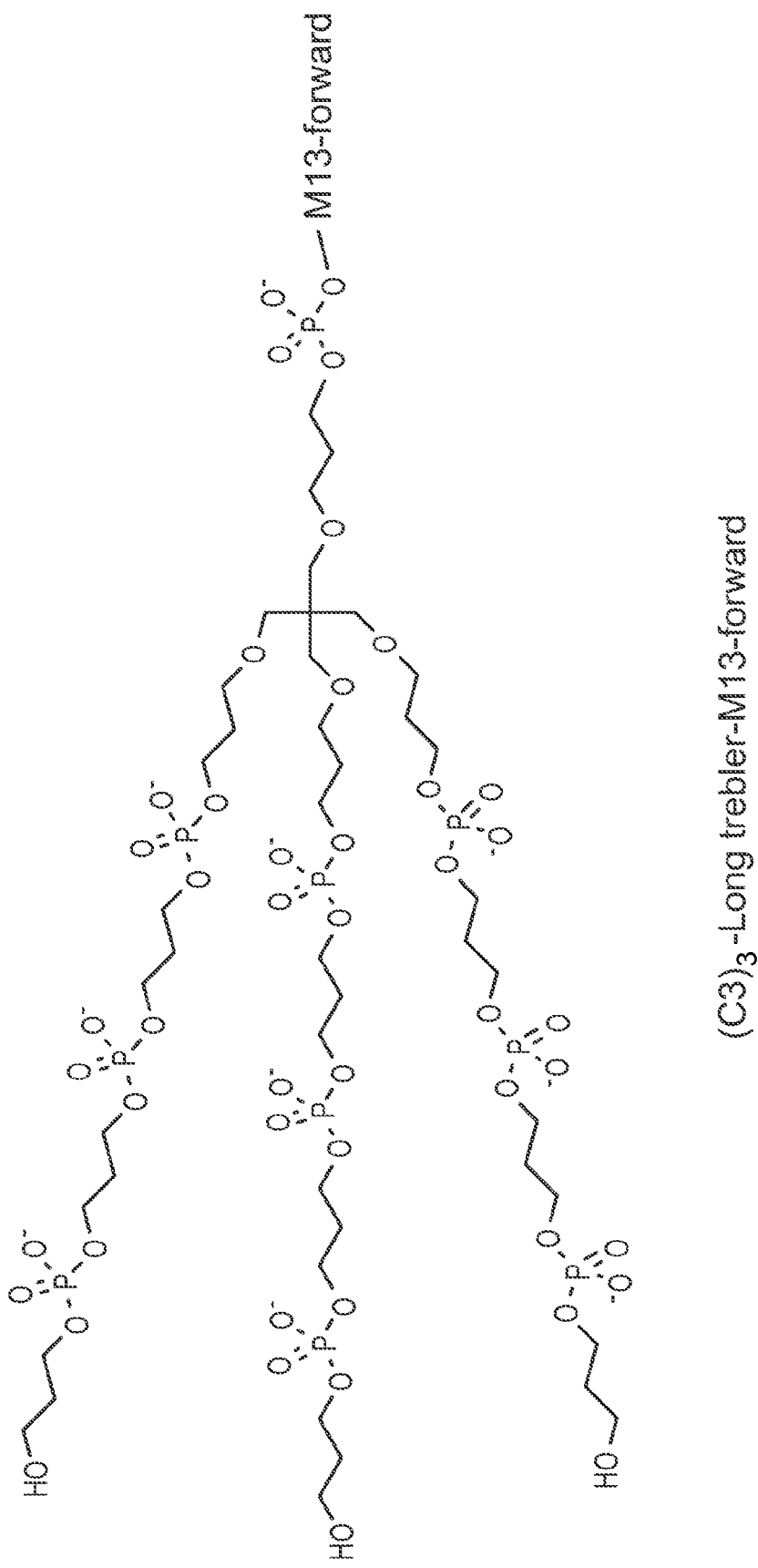
FIG. 3F illustrates a chemically-enhanced primer consisting of $(C3)_3$-Long trebler-M13 (Forward).
Figure 3G:
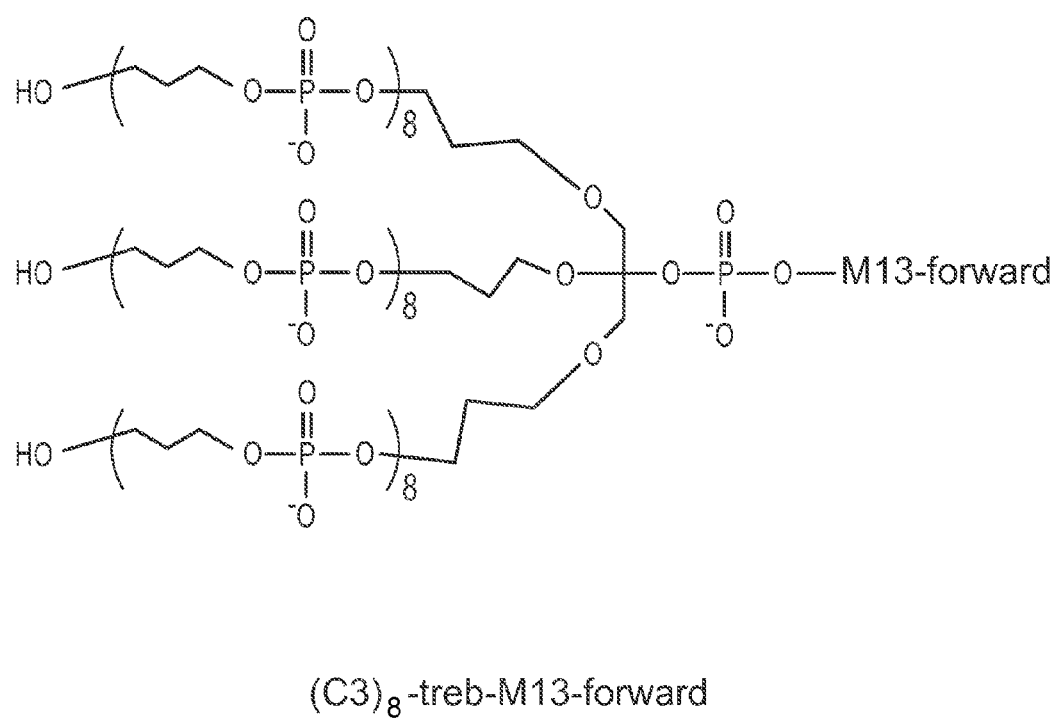
FIG. 3G illustrates a chemically-enhanced primer consisting of $(C_3)_8$-treb-M13 (Forward).
Figure 3H:
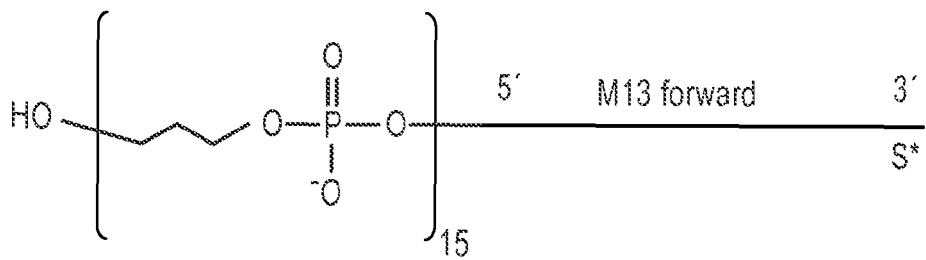
FIG. 3H illustrates a chemically-enhanced primer consisting of $(C3)_{15}$-M13* (Forward), * indicates a phosphorothioate linkage.
Figure 3I:
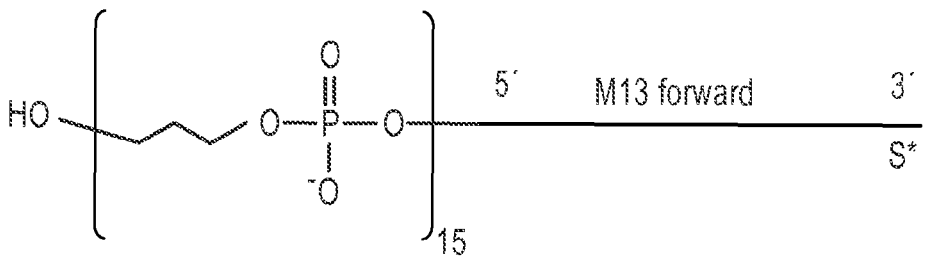
FIG. 3I illustrates a chemically-enhanced primer consisting of $(C3)_{15}$-M13*(Forward), * indicates a phosphorothioate linkage.

Sequencing Workflow with a Chemically Enhanced Primer Having a Phosphorothioate (PS) Linkage Sequencing reaction prepared with the BigDye Direct Cycle Sequencing Kit (24 reactions, P/N 4458689, Applied Biosystems): 10 μL of the PCR amplification reaction was mixed with 2 μL BigDye® Direct Sequencing Master Mix (P/N 4458701, Applied Biosystems), and 1 μL BigDye Direct M13 Forward Primer (P/N 4458692 Applied Biosystems) or BigDye Direct M13 Reverse Primer 4458695, Applied Biosystems). The BigDye Direct Primers have the terminal 5' NCM and a terminal 3' PS. The cycle sequencing reaction was carried out on a Verti 96-well thermal cycler at 37° C. 15 min. at which point excess PCR amplification primers were digested by the ExoI nuclease (contained in the BigDye Direct Sequencing Master Mix), then 80° C. 2 min, 96° C. 1 min. followed by 25 cycles, of 96° C. 10 seconds, 50° C. 5 seconds, and 60° C. 1 minute 15 seconds and 4° C. hold. The Sequencing primer contained a terminal 5' Negatively Charged Moiety (NCM) and a terminal 3' phosphorothioate group indicated by an asterisk: M13 forward primer (1 μM) (NCM-TGTAAAACGACGGCCAG*T) (SEQ ID NO:4) or M13 reverse primer (1 μM) (NCM-CAGGAAACAGCTATGAC*C) (SEQ ID NO:5). FIG. 3H provides the structure of the NCM. FIG. 11 is a electropherogram (see U.S. Ser. No. 61/407,899, filed Oct. 28, 2011 and U.S. Ser. No. 61/408,553, filed Oct. 29, 2011), of a chemically-enhanced primer (FIG. 3H) with a terminal 3' PS linkage and ZC as the template. The sequence of ZC shows high resolution at base 1 from the primer.

Example 3

PCR reactions were carried out in the following 10 μL solution: to sequence amplicon RSA000317141 (Template Seq01, 545 bp), 1 μL 4 ng/μL gDNA, M13-tagged primers (0.8 uM each): 1.5 μL of TGTAAAACGACGGCCAGT-GCTGCCTCTGATGGCGGAC (SEQ ID NO:6, forward, gnl|Probe|1204459b) and CAGGAAACAGCTATGAC-CGCCACACTCTGGAGCTGGACA (SEQ ID NO:7, reverse, gnl|Probe|1204459c), 5 μL of BigDye Direct PCR Master Mix (P/N 4458699, Applied Biosystems) and 2.5 μL water. PCR was carried out on a Veriti™ 96-well thermal cycler (P/N 4375786, Applied Biosystems). with the following thermal cycling conditions: 95° C. for 10 minutes, then 35 cycles of 96° C. for 3 seconds, 62° C. for 15 seconds, and 68° C. for 30 sec. followed by 72° C. for 2 min. and 4° C. hold. To confirm amplification a 10 μL sample was analyzed on an agarose gel. A band consistent with the expected 545 bp amplicon was observed.

Amplicon RSA000317141 SEQ ID NO:8, template Seq01 (FIG. 3I) is shown below with primer binding sites for PCR forward primer, and PCR reverse primer (reverse complement) underlined.

```
TGTAAAACGACGGCCAGTGCTGCCTCTGATGGCGGACGGGGGTGTGG

TCCTGGGACTCGTGGTCAGGGCTGGTCTGTGTGGAATGCTGATCCTT

CTCTTCCCCAATCTACCTGTGTCAGTTCCCTCCTTTTCTATTTTCTC

TTCCCTGCAGATGTCAAGCCCTCCAACATCCTAGTCAACTCCCGTGG

GGAGATCAAGCTCTGTGACTTTGGGGTCAGCGGGCAGCTCATCGACT

CCATGGCCAACTCCTTCGTGGGCACAAGGTCCTACATGTCGGTATGA

ACAGAAGTTTCCATTGCTTGAGCTTCTTGTACGGTCAGGGAGAGGAG

CCCAGTGGGTGCCTTTCCTGTGGAGCCAGAGTCTTGTGCTGGGTAGG

GGACAAGAAGTGAGGGAGGAGGCACAGTGCTCTGCCCTGAGGAGATG

AAGTTGAATGGGAAGATGGTCTTGGTCTTTCTTAGGCCTTGGAGCAT

AACTGGGATATTGGGGCCTTGACTCACTGAAAGGACTGTCCAGCTCC

AGAGTGTGGCGGTCATAGCTGTTTCCTG.
```

Sequencing Workflow with a Chemically-Enhanced Primer Having a Phosphorothioate (PS) Linkage.

Figure 3J:
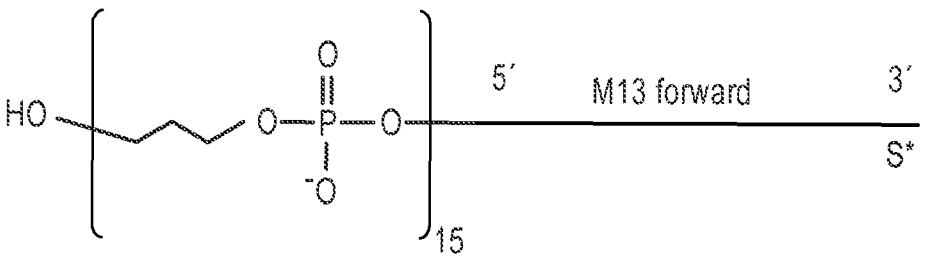
FIG. 3J illustrates a chemically-enhanced primer consisting of $(C3)_{15}$-M13* (Forward), * indicates a phosphorothioate linkage
Figure 4A:
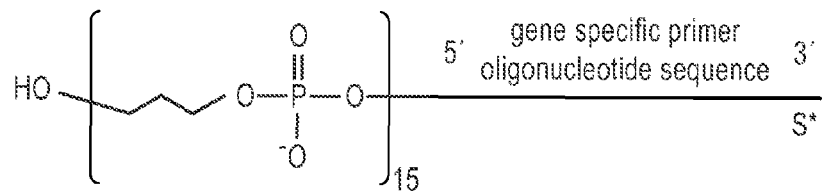
FIG. 4A-4B illustrates a chemically-enhanced primer consisting of $(C3)_{15}$-gene specific primer oligonucleotide sequence* (Forward) or a universal primer oligonucleotide sequence* (Forward), respectively, indicates a phosphorothioate linkage.
Figure 4B:
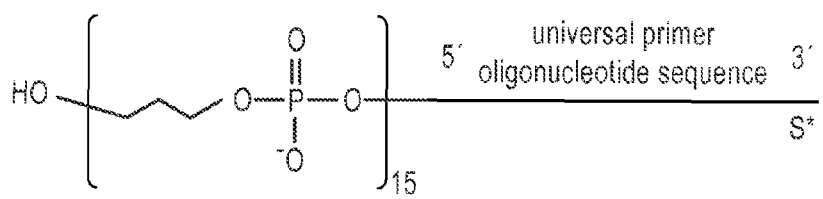
Figure 4C:
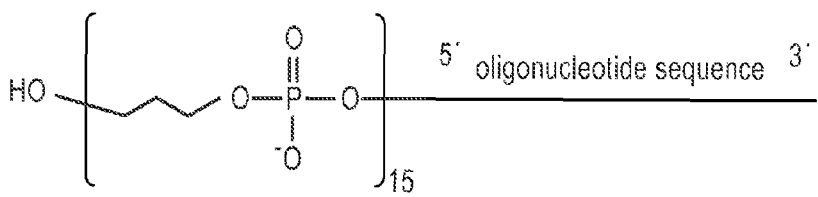
FIG. 4C illustrates a chemically-enhanced primer consisting of $(C3)_{15}$-oligonucleotide sequence (Forward).

Sequencing reaction prepared with the BigDye Direct Cycle Sequencing Kit (24 reactions, P/N 4458689, Applied Biosystems): 10 μL of the PCR amplification reaction was mixed with 2 μL BigDye® Direct Sequencing Master Mix (P/N 4458701, Applied Biosystems), and 1 μL BigDye Direct M13 Forward Primer (P/N 4458692 Applied Biosystems) or BigDye Direct M13 Reverse Primer 4458695, Applied Biosystems). The BigDye Direct Primers have the terminal 5' NCM and a terminal 3' PS. The cycle sequencing reaction was carried out on a Verti 96-well thermal cycler at 37° C. 15 min. at which point excess PCR amplification primers were digested by the ExoI nuclease (contained in the BigDye Direct Sequencing Master Mix), then 80° C. 2 min, 96° C. 1 min. followed by 25 cycles, of 96° C. 10 seconds, 50° C. 5 seconds, and 60° C. 1 minute 15 seconds and 4° C. hold. The Sequencing primer contained a terminal 5' Negatively Charged Moiety (NCM) and a terminal 3' phosphorothioate group indicated by an asterisk: M13 forward primer (1 μM) (NCM-TGTAAAACGACGGCCAG*T) (SEQ ID NO:4) or M13 reverse primer (1 μM) (NCM-CAGGAAACAGCTATGAC*C) (SEQ ID NO:5). FIG. 16 (see U.S. Ser. No. 61/408,553, filed Oct. 29, 2011), provides a electropherogram of a chemically-enhanced primer with a terminal 3' PS linkage and RSA000317141 as the template (FIG. 3J). The sequence of RSA000317141 shows high resolution at base 1 from the primer.

Example 4

PCR and Sequencing Reactions with or without PS Linkage: Standard PCR Amplification: PCR reactions were carried out in the following 10 μL solution: for example to sequence amplicon RSA0003176671 μL 10 ng/μL gDNA, primers (0.8 uM each), 1.5 μL of TGTAAAACGACGGC- CAGTGGCTCCTGGCACAAAGCTGG (gnl|Probe|1172813b, forward, SEQ ID NO:9) and CAG-GAAACAGCTATGACCTGCATCTCATTCTCCAG-GCTTC (gnl|Probe|1172813c, reverse, SEQ ID NO:10),), 5 µL of AmpliTaq Gold® PCR Master Mix (P/N 4318739, Applied Biosystems), 1.6 µL 50% glycerol and 0.9 µL water. PCR was carried using a Gold-plated 96-Well GeneAmp® PCR System 9700 (P/N 4314878, Applied Biosystems). Thermal cycling conditions: 96° C. 5 minutes, then 40 cycles of 94° C. 30 seconds, 60° C. 45 seconds, and 72° C. 45 sec. followed by 72° C. 2 min. and 4° C. hold. A 5 µL aliquot was analyzed on an agarose gel. A band consistent with the expected 630 bp amplicon was observed.

PCR Clean-Up:

The 10 µL of PCR amplification reaction was mixed with 2 µL of ExoSAP-IT® nuclease (P/N 78250, Affymetrix, Santa Clara, Calif.) and incubated on a Gold-plated 96-Well GeneAmp® PCR System 9700 (P/N 4314878, Applied Biosystems) at 37° C. 30 minutes followed by 80° C. for 15 minutes (inactivated the nuclease.

Sequencing Workflow with a Chemically-Enhanced Primer without Phosphorothioate Linkage A sequencing reaction was prepared with the BigDye® Terminator v3.1 Cycle Sequencing Kit (24 reactions, P/N 4337454, Applied Biosystems): 2 µL of the PCR amplification reaction treated with ExoSAP-IT was mixed with 4 µL BigDye® Terminator v3.1 Cycle Sequencing Kit Master Mix (P/N 4337454, Applied Biosystems), 1 µL Sequencing primers chemically-enhanced with terminal 5' NCM and with or without a terminal 3' phosphorothioate linkage, (NCM-M13 forward and NCM-M13 reverse primer) and 3 µL water. The cycle sequencing reaction was carried out at 96° C. 1 min. followed by 25 cycles, 96° C. 10 sec. 50° C. 5 sec, 60° C. 1 min. 15 sec followed by 4° C. hold. For example, the sequencing primer is M13 forward primer (1 µM) containing a terminal 3' phosphorothioate (PS) group indicated by an asterisk (NGM-TGTAAAACGACGGCCAG*T) (SEQ ID NO:4), M13 reverse primer (1 µM) (NGM-CAGGAAACAGCTATGAC*C) (SEQ ID NO:5) or without PS, M13 forward primer (1 µM) (NGM-TGTAAAAC-GACGGCCAGT) (SEQ ID NO:11), M13 reverse primer (1 µM) (NGM-CAGGAAACAGCTATGACC) (SEQ ID NO:12). FIGS. 4 and 8 provide electropherograms (see U.S. Ser. No. 61/407,899, filed Oct. 28, 2011 and U.S. Ser. No. 61/408,553, filed Oct. 29, 2011), of chemically-enhanced sequencing primers (FIGS. 3A and 3F, respectively), with terminal 5' negatively charged moieties, without PS and RSA000317667 as the template. The sequences for RSA000317667 show high resolution at base 1 from the primer.

Example 5

Capillary Electrophoresis Sample Preparation and Detection

The amplified samples are analyzed by methods that resolve nucleobase sequences as would be known to one of skill in the art. For example, capillary electrophoresis can be used following the instrument manufactures directions. Big-Dye XTerminator Purification Kit (Applied Biosystems, P/N 4376486) can be used in cycle sequencing clean up to prevent the co-injection of un-incorporated dye-labeled terminators, dNTPs and salts with dye-labeled extension products into a capillary electrophoresis DNA analyzer. Briefly, 13 µL sequencing reaction mixture was combined with 45 µL SAM Solution and 10 µL XTerminator Solution. After vortexing the sample plate at 1800 rpm for 20 minutes, spin the plate at 1000×g for 2 minutes. To each well was added 30 µL of 70% ethanol and the plate was centrifuged at 1650×g for 15 minutes. The solution was removed by inverting the plate onto a paper towel and centrifuging at 180×g for 1 minute. The precipitated sequencing reaction was then dissolved in 10 µL of 50 µM EDTA and loaded onto an AB 3500xL Genetic Analyzer equipped with a 50 cm capillary array (Applied Biosystems, Foster City, Calif.).

Example 6

Capillary Electrophoresis Methods and Analysis

Capillary electrophoresis (CE) was performed on the current Applied Biosystems instruments, for example the Applied Biosystems 3500×1 Genetic Analyzer, using the dye set Z as described the instrument's User Guide. There are ShortReadSeq_BDX_POP7, RapidSeq_BDX_POP7, FastSeq_BDX_POP7, StdSeq_BDX_POP7 run modules. For example, BDxFastSeq50_POP7xl_1 parameters were: oven temperature: 60 C, sample injection for 5 sec at 1.6 kV and electrophoresis at 13.4 kV for 2520 sec in Performance Optimized Polymer (POP-7™ polymer) with a run temperature of 60° C. Variations in instrument parameters, e.g. injection conditions, were different on other CE instruments such as the 3500 or 3730xl Genetic Analyzers. The data were collected using versions the Applied Biosystems Data Collection Software specific to the different instruments, such as 3500 Data Collection Software v1.0. The sequence traces were analyzed by Applied Biosystems KB™ Basecaller Software v1.4.1 with KB_3500_POP7_BDTv3direct.bcc and KB_3500_POP7_BDTv3direct.mob to determine the correct base calls.

Example 7

Sequencing of Plasmid DNA or PCR Amplified Exo/SAP Treated DNA 200 ng of pGem plasmid DNA or 10 ng of Exo/SAP treated PCR product mixed with BigDye Terminator v3.1 Ready Reaction reagent and sequencing primer having an NCM composition without PS was reacted in a cycle sequencing reaction: 95 C/1 min and 25 cycles of (96 C/1 min, 50 C/5 sec, 60 C/1 min 15 sec). The reaction was cleaned up using BigDye XTerminator Kit (Applied Biosystems) and electrophrosesed on the 3500 with POP7 polymer. The electropherogram of the sequenced pGEM plasmid sequenced using the sequencing primer having NCM on the 5' indicated clear sequence within five base pairs of the primer (data not shown). The electropherogram of the sequenced pGEM plasmid sequenced using the sequencing primer having NCM on the 5' and nuclease resistance linkage on the 3' end indicated clear sequence five base pairs after the primer (data not shown). The electropherogram of the Exo/SAP treated PCR product sequenced using the sequencing primer with NCM on the 5' and nuclease resistance linkage on the 3' end indicated clean sequence reads six bases after the primer (data not shown).

Those skilled in the art understand that the detection techniques employed are generally not limiting. Rather, a wide variety of detection means are within the scope of the disclosed methods and kits, provided that they allow the presence or absence of an amplicon to be determined.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

We claim:

1. A method for sequencing DNA, comprising the steps of:
   a. amplifying DNA in a first reaction mixture comprising nuclease-sensitive amplification primers to form amplified DNA;
   b. contacting the first reaction mixture of the amplifying step with a second reaction mixture comprising a nuclease and a chemically-enhanced primer, the chemically-enhanced primer comprises an oligonucleotide sequence having a nuclease resistance inter-nucleotide linkage and a negatively charged moiety (NCM), and the NCM comprises a moiety having a structure of the following formula:

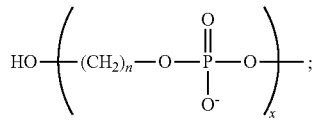

wherein each n is independently an integer of 1 to 9, and x is an integer of 2 to about 30;
   c. inactivating the nuclease; and
   d. reacting the amplified DNA in a sequencing reaction wherein the chemically-enhanced primer primes the sequencing reaction.

2. The method of claim 1, further comprising:
   obtaining sequencing results based on the sequencing reaction; and
   determining a nucleotide base sequence of the amplified DNA based on the results.

3. The method of claim 1, wherein amplifying DNA comprises the step of polymerase chain reaction amplification.

4. The method of claim 1, wherein the nuclease is selected from exonuclease I, Exo III, Pfu and DNA pol I.

5. The method of claim 1, wherein the chemically-enhanced primer has structure of Formula I:

Formula I

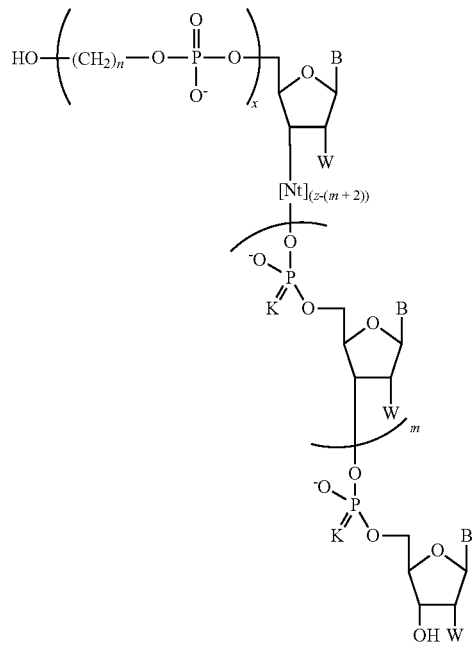

wherein B is a nucleobase;
K is S or O;
each instance of n is independently an integer of 1 to 9;
m is 0 or 1;
x is an integer of 2 to about 30;
z is an integer of 3 to about 100;
W is OH, F, OMe, or H; and Nt is a moiety having a formula:

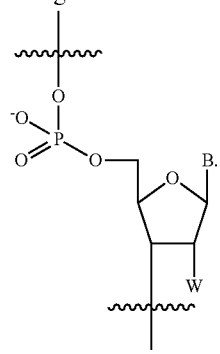

6. The method of claim 1, wherein the chemically-enhanced primer has a structure of the formula:
$(Cn)_x$-OLIGO, wherein $(Cn)_x$ has a structure of the following formula:

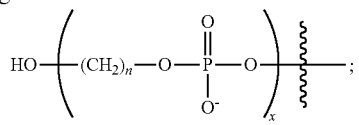

wherein each instance of n is independently an integer of 1 to 9; and x is an integer of 2 to about 30;
OLIGO has a structure of the following formula:

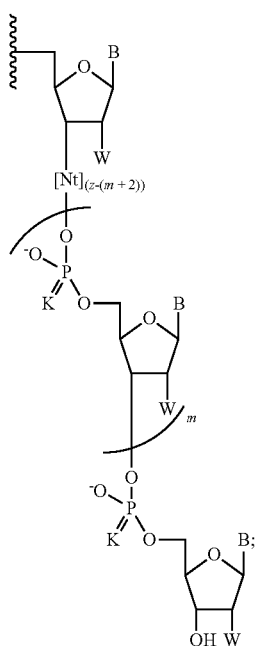

wherein B is a nucleobase;

K is S or O;

m is 0 or 1;

z is an integer of 3 to about 100;

W is OH, F, OMe, or H; and

Nt is a moiety having a formula:

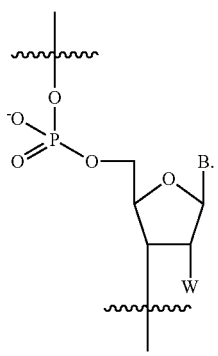

7. The method of claim 1, wherein the chemically-enhanced primer comprises one nuclease-resistant linkage at a terminal 3' end.

8. The method of claim 1, wherein the sequencing reaction comprises cycle sequencing.

9. The method of claim 1, wherein the chemically-enhanced primer comprises a plurality of NCMs either at a terminal 5' end or within an oligonucleotide sequence of the chemically-enhanced primer.

* * * * *

SEQUENCE LISTING

<160> NUMBER OF SEQ ID NOS: 12

<210> SEQ ID NO 1
<211> LENGTH: 39
<212> TYPE: DNA
<213> ORGANISM: Artificial Sequence
<220> FEATURE:
<223> OTHER INFORMATION: Forward Primer

<400> SEQUENCE: 1
tgtaaaacga cggccagttt gatgggctca gcaacaggt                     39

<210> SEQ ID NO 2
<211> LENGTH: 40
<212> TYPE: DNA
<213> ORGANISM: Artificial Sequence
<220> FEATURE:
<223> OTHER INFORMATION: Reverse Primer

<400> SEQUENCE: 2
caggaaacag ctatgacccc actgcttgcg tttcttcctg                    40

<210> SEQ ID NO 3
<211> LENGTH: 626
<212> TYPE: DNA
<213> ORGANISM: Artificial Sequence
<220> FEATURE:
<223> OTHER INFORMATION: Template

<400> SEQUENCE: 3
caggaaacag ctatgacccc actgcttgcg tttcttcctg ttttaatccc actttcaatg      60
aagtgtgtat ttgaaataaa tggctcatga gttaatcaca tctttatata tcctaagatg    120
tattacaaag gcttccataa cacttgtcta tagtaagcca ctcatttcta taattttct     180 ttcaataaac tcaatctttg taatacagaa attaaccttc tgggttgttt tgttcaaga    240 tcttcagttt gatttgcccc ttggttgatc tgttttccc atcgctgaac tggttcccat    300
aatcacacac ctttgctttt catttccaca gatcaaggaa tcaacattta ccgaaagcca    360
cccatctaca aacagcatgg taaaacccgc tttcctccgc gtagcttta aatagcaaag    420 tcagctgaac ttctccttgc tgtcctctga aaggcttttc ctgctgctgc ttttgagagt    480
aaaactgggg catccagcat attatgcctt tctggtctac taagatgtaa atattgtaaa    540
attgattctc ctggatggag agacttagct tgattagaaa gcttctaacc tgttgctgag    600
cccatcaaac tggccgtcgt tttaca                                         626

<210> SEQ ID NO 4
<211> LENGTH: 18
<212> TYPE: DNA
<213> ORGANISM: Artificial Sequence
<220> FEATURE:
<223> OTHER INFORMATION: Forward Primer

<400> SEQUENCE: 4
tgtaaaacga cggccagt                                             18

<210> SEQ ID NO 5
<211> LENGTH: 18
<212> TYPE: DNA
<213> ORGANISM: Artificial Sequence
<220> FEATURE:
<223> OTHER INFORMATION: Reverse Primer

<400> SEQUENCE: 5
caggaaacag ctatgacc                                                            18

<210> SEQ ID NO 6
<211> LENGTH: 37
<212> TYPE: DNA
<213> ORGANISM: Artificial Sequence
<220> FEATURE:
<223> OTHER INFORMATION: Forward Primer

<400> SEQUENCE: 6
tgtaaaacga cggccagtgc tgcctctgat ggcggac                                        37

<210> SEQ ID NO 7
<211> LENGTH: 39
<212> TYPE: DNA
<213> ORGANISM: Artificial Sequence
<220> FEATURE:
<223> OTHER INFORMATION: Reverse Primer

<400> SEQUENCE: 7
caggaaacag ctatgaccgc cacactctgg agctggaca                                      39

<210> SEQ ID NO 8
<211> LENGTH: 545
<212> TYPE: DNA
<213> ORGANISM: Artificial Sequence
<220> FEATURE:
<223> OTHER INFORMATION: Synthetic DNA

<400> SEQUENCE: 8
tgtaaaacga cggccagtgc tgcctctgat ggcggacggg ggtgtggtcc tgggactcgt          60
ggtcagggct ggtctgtgtg gaatgctgat ccttctcttc cccaatctac ctgtgtcagt         120
tccctccttt tctatttctt cttccctgca gatgtcaagc cctccaacat cctagtcaac         180
tcccgtgggg agatcaagct ctgtgacttt ggggtcagcg ggcagctcat cgactccatg         240
gccaactcct tcgtgggcac aaggtcctac atgtcggtat gaacagaagt ttccattgct         300
tgagcttctt gtacggtcag ggagaggagc ccagtgggtg cctttcctgt ggagccagag         360
tcttgtgctg ggtaggggac aagaagtgag ggaggaggca cagtgctctg ccctgaggag         420
atgaagttga atgggaagat ggtcttggtc tttcttaggc cttggagcat aactgggata         480
ttggggcctt gactcactga aaggactgtc cagctccaga gtgtggcggt catagctgtt         540
tcctg                                                                    545

<210> SEQ ID NO 9
<211> LENGTH: 38
<212> TYPE: DNA
<213> ORGANISM: Artificial Sequence
<220> FEATURE:
<223> OTHER INFORMATION: Forward Primer

<400> SEQUENCE: 9
tgtaaaacga cggccagtgg ctcctggcac aaagctgg                                       38

```
<210> SEQ ID NO 10
<211> LENGTH: 40
<212> TYPE: DNA
<213> ORGANISM: Artificial Sequence
<220> FEATURE:
<223> OTHER INFORMATION: Reverse Primer

<400> SEQUENCE: 10
caggaaacag ctatgacctg catctcattc tccaggcttc                              40

<210> SEQ ID NO 11
<211> LENGTH: 18
<212> TYPE: DNA
<213> ORGANISM: Artificial Sequence
<220> FEATURE:
<223> OTHER INFORMATION: M13 Forward Primer

<400> SEQUENCE: 11
tgtaaaacga cggccagt                                                      18

<210> SEQ ID NO 12
<211> LENGTH: 18
<212> TYPE: DNA
<213> ORGANISM: Artificial Sequence
<220> FEATURE:
<223> OTHER INFORMATION: M13 Reverse Primer

<400> SEQUENCE: 12
caggaaacag ctatgacc                                                      18
```